US006384041B1

(12) United States Patent
Hutchison et al.

(10) Patent No.: US 6,384,041 B1
(45) Date of Patent: May 7, 2002

(54) BICYCLIC SPLA$_2$ INHIBITORS

(75) Inventors: Darrell Robert Hutchison, Indianapolis; Michael John Martinelli, Zionsville; Thomas Michael Wilson, Speedway, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/719,318

(22) PCT Filed: Jun. 23, 1999

(86) PCT No.: PCT/US99/14213

§ 371 Date: Dec. 11, 2000

§ 102(e) Date: Dec. 11, 2000

(87) PCT Pub. No.: WO00/00201

PCT Pub. Date: Jan. 6, 2000

Related U.S. Application Data

(60) Provisional application No. 60/091,248, filed on Jun. 30, 1998.

(51) Int. Cl.$^7$ ............... A61K 31/505; A61K 31/535; C07D 413/12; C07D 487/04
(52) U.S. Cl. ................................ 514/258; 544/280
(58) Field of Search ..................... 544/280; 514/258

(56) References Cited

U.S. PATENT DOCUMENTS

| 3,867,386 A | 2/1975 | Kim et al. ............ 260/256.4 F |
| 5,916,922 A | 6/1999 | Goodson, Jr. et al. ...... 514/563 |

*Primary Examiner*—Bruck Kifle
(74) *Attorney, Agent, or Firm*—Roger S. Benjamin

(57) ABSTRACT

The compounds are of the class of pyrrolo[2,3-d]pyrimidines useful for inhibiting sPLA$_2$ mediated release of fatty acids for treatment of diseases such as septic shock.

13 Claims, No Drawings

BICYCLIC SPLA₂ INHIBITORS

This application is a 371 of PCT/US99/14213, filed Jun. 23, 1999, and claims benefit of No. 60/091,248, filed Jun. 30, 1998.

This invention relates to novel pyrrolo[2,3-d]-pyrimidines useful for inflammatory diseases.

The structure and physical properties of human non-pancreatic secretory phospholipase $A_2$ (hereinafter called, "sPLA₂") has been thoroughly described in two articles, namely, "Cloning and Recombinant Expression of Phospholipase $A_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase $A_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

It is believed that sPLA₂ is a rate limiting enzyme in the arachidonic acid cascade which hydrolyzes membrane phospholipids. Thus, it is important to develop compounds which inhibit sPLA₂ mediated release of fatty acids (e.g., arachidonic acid). Such compounds would be of value in general treatment of conditions induced and/or maintained by overproduction of sPLA₂; such as sepsis or rheumatoid arthritis.

It is desirable to develop new compounds and treatments for sPLA₂ induced diseases.

This invention is a novel use of the class of compounds known as pyrrolo[2,3-d]pyrimidines to inhibit mammalian sPLA₂ mediated release of fatty acids.

This invention Is also a novel class of pyrrolo[2,3-d] pyrimidines having potent and selective effectiveness as inhibitors of mammalian sPLA₂.

This invention is also a pyrrolo[2,3-d]pyrimidine compound in the treatment of Inflammatory Disease.

This invention is also pharmaceutical compositions containing the pyrrolo[2,3-d]pyrimidines of the invention.

This invention is also a method of preventing and treating Inflammatory Diseases in mammals by contact with a therapeutically effective amount of the pyrrolo[2,3-d] pyrimidines of the invention.

This invention is also the use, in the manufacture of a medicament of pyrrolo[2,3-d]pyrimidine compound as an active ingredient in an sPLA₂ inhibiting composition in admixture with an inert carrier.

Definitions

The term, "Inflammatory Diseases" refers to diseases such as inflammatory bowel disease, sepsis, septic shock, adult respiratory distress syndrome, pancreatitis, trauma-induced shock, bronchial asthma, allergic rhinitis, rheumatoid arthritis, cystic fibrosis, stroke, acute bronchitis, chronic bronchitis, acute bronchiolitis, chronic bronchiolitis, osteoarthritis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit sPLA₂ mediated release of fatty acid and to thereby inhibit or prevent the arachidonic acid cascade and its deleterious products.

The term, "pyrrolo[2,3-d]pyrimidine nucleus" refers to a nucleus (having numbered positions)with the structural formula (X):

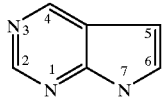

(X)

The pyrrolo[2,3-d]pyrimidine compounds of the invention employ certain defining terms as follows:

The term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, n-pentyl, and n-hexyl.

The term, "alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers.

The term, "hydrocarbyl" means an organic group containing only carbon and hydrogen.

The term, "halo" means fluoro, chloro, bromo, or iodo.

The term, "heterocyclic radical", refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiopheneyl, pentamethylenesulfadyl, 1,3-dithianyl, 1,4-dithianyl, 1,4-thioxanyl, azetidinyl, hexamethyleneiminium, heptamethyleneiminium, piperazinyl and quinoxalinyl.

The term, "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, thiophenyl, naphthyl, norbornanyl, bicycloheptadienyl, toluoyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (a):

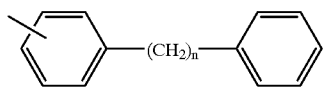

(a)

where n is a number from 1 to 8.

The term, "non-interfering substituent", refers to radicals suitable for substitution at the 2 position of the pyrrolo[2,3-d]pyrimidine nucleus and on other nucleus substituents (as hereinafter described for Formula I), infra. Illustrative non-interfering radicals are $C_1$–$C_8$ alkyl, $C_2$–$C_8$ alkenyl, $C_2$–$C_8$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, toluoyl, xylenyl, biphenyl, $C_1$–$C_8$ alkoxy, $C_2$–$C_8$ alkenyloxy, $C_2$–$C_8$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_1$–$C_{12}$ alkoxyamino, $C_2$–$C_{12}$ alkoxyaminocarbonyl, $C_1$–$C_{12}$ alkylamino, $C_1$–$C_8$ alkylthio, $C_2$–$C_{12}$ alkylthiocarbonyl, $C_1$–$C_8$ alkylsulfinyl, $C_1$–$C_8$ alkylsulfonyl, $C_1$–$C_8$ haloalkoxy, $C_1$–$C_8$ haloalkylsulfonyl, $C_1$–$C_8$ haloalkyl, —$CF_3$, $C_1$–$C_8$ hydroxyalkyl, —C(O)O($C_1$–$C_8$ alkyl), —$(CH_2)_n$—O—($C_1$–$C_8$ alkyl), benzyloxy, phenoxy, phenylthio, —(CONHSO$_2$R), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_8$ carbonyl; where n is from 1 to 8.

The term, "(acidic group)" means an organic group which when attached to a pyrrolo[2,3-d]pyrimidine nucleus, through suitable linking atoms (hereinafter defined as the "acid linker"), acts as a proton donor capable of hydrogen bonding. Illustrative of an (acidic group) are the following:

-5-tetrazolyl,

—$SO_3H$,

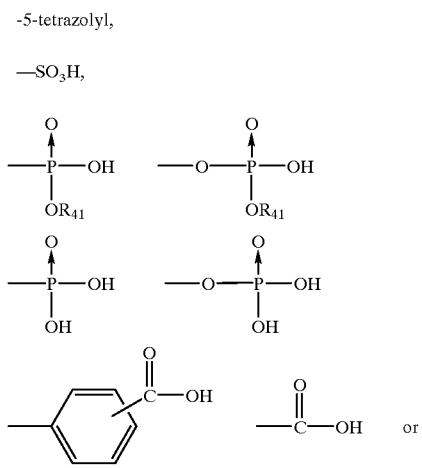

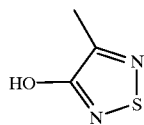

where n is 1 to 8, $R_{41}$ is a metal or $C_1$–$C_8$ alkyl.

The words, "acid linker" refer to a divalent linking group symbolized as, —(La)—, which has the function of joining the 4 or 5 position of the pyrrolo[2,3-d]pyrimidine nucleus to an acidic group in the general relationship:

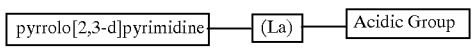

The words, "acid linker length", refer to the number of atoms (excluding hydrogen) in the shortest chain of the linking group —(La)— that connects the 4 position of the pyrrolo[2,3-d]pyrimidine nucleus with the acidic group. The presence of a carbocyclic ring in —(La)— counts as the number of atoms approximately equivalent to the calculated diameter of the carbocyclic ring. Thus, a benzene or cyclohexane ring in the acid linker counts as 2 atoms in calculating the length of —(La)—. Illustrative acid linker groups are;

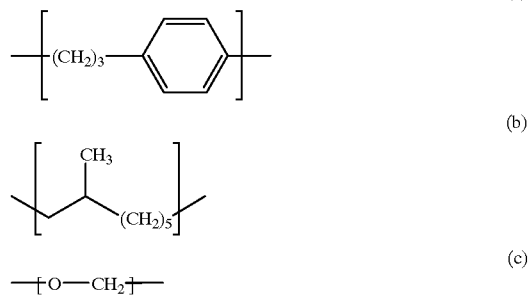

wherein, groups (a), (b), and (c) have acid linker lengths of 5, 7, and 2, respectively.

The term, "amine", includes primary, secondary and tertiary amines.

The terms, "mammal" and "mammalian" include human.

The term, "alkylene chain of 1 or 2 carbon atoms" refers to the divalent radicals, —$CH_2$—$CH_2$— and —$CH_2$—.

The term, "group containing 1 to 4 non-hydrogen atoms" refers to relatively small groups which form substituents at the 6 position of the pyrrolo[2,3-d]pyrimidine nucleus, said groups may contain non-hydrogen atoms alone, or non-hydrogen atoms plus hydrogen atoms as required to satisfy the unsubstituted valence of the non-hydrogen atoms, for example; (i) groups absent hydrogen which contain less than 4 non-hydrogen atoms such as —$CF_3$, —Cl, —Br, —$NO_2$, —CN, —$SO_3$; and (ii) groups having hydrogen atoms which contain less than 4 non-hydrogen atoms such as —$CH_3$, —$C_2H_5$, and —CH=$CH_2$.

The Pyrrolo[2,3-d]pyrimidine Compounds of the Invention

The compounds of the invention have the general formula (I) or a pharmaceutically acceptable salt, solvate or prodrug thereof;

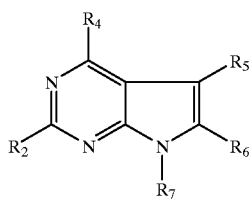

(I)

wherein;
  $R_2$ is selected from hydrogen, non-interfering substituent, carbocyclic radical, carbocyclic radical substituted with non-interfering substituent(s), heterocyclic radicals, and heterocyclic radical substituted with non-interfering substituent(s);
  $R_4$ is —($L_4$)-(acidic group); wherein —($L_4$)—, is a divalent acid linker having an acid linker length of 1 to 4;
  $R_5$ is —($L_5$)—Z, where —($L_5$)— is a divalent linker group selected from a bond or a divalent group selected from:

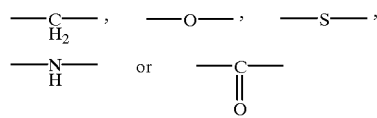

and Z is selected from acetamide, thioacetamide, glyoxylamide, thioglyoxylamide, hydrazide or thiohydrazide groups represented by the formulae,

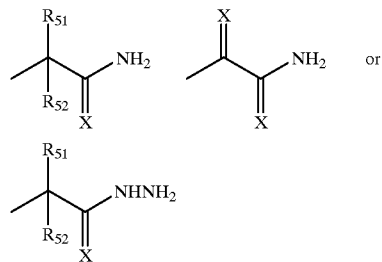

where
  $R_{51}$ and $R_{52}$ are independently selected from hydrogen, $C_1$–$C_8$ alkyl, $C_1$–$C_8$ haloalkyl, and $C_3$–$C_4$ cycloalkyl, and X is oxygen or sulfur;
  $R_6$ is hydrogen, or a group containing 1 to 4 non-hydrogen atoms plus any required hydrogen atoms;
  $R_7$ is selected from groups (a), (b) and (c) wherein;
    (a) is $C_7$–$C_{20}$ alkyl, $C_7$–$C_{20}$ haloalkyl, $C_7$–$C_{20}$ alkenyl, $C_7$–$C_{20}$ alkynyl, carbocyclic radical, or heterocyclic radical, or
    (b) is a member of (a) substituted with one on more independently selected non-interfering substituents; or
    (c) is the group —($L_7$)—$R_{71}$; where, —($L_7$)— is a divalent linking group of 1 to 12 atoms selected from carbon, hydrogen, oxygen, nitrogen, and sulfur; wherein the combination of atoms in —($L_7$)— is selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where $R_{71}$ is a group selected from (a) or (b).

Preferred Subgroups of Compounds of Formula (I)

I. Preferred $R_2$ Substituents $R_2$ is preferably selected from the group consisting of hydrogen, cyclopropyl, $C_1$–$C_8$ alkyl, $C_1$–$C_8$ haloalkyl, $C_1$–$C_8$ alkoxy, $C_1$–$C_8$ thioalkyl, $C_1$–$C_8$ alkylsulfonyl, $C_1$–$C_{12}$ alkylamino, phenyl, and thiophenyl. Particularly preferred $R_2$ groups are hydrogen, methyl, ethyl, propyl, isopropyl, —S—$CH_3$, —S—$C_2H_5$, methylsulfonyl, ethylsulfonyl, thiophenyl, dimethylamino, diethylamino, ethylamino, methoxy, and ethoxy.

II. Preferred $R_4$ Substituents

A preferred subclass of compounds of formula (I) are those wherein $R_4$ is a substituent having an acid linker with an acid linker length of 2 or 3 and the acid linker group, —($L_4$)—, is selected from a group represented by the formula;

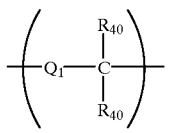

where Q1 is selected from the group —($CH_2$)—, —O—, —NH—, —C(O)—, —S—, and

and where $R_{40}$ is independently selected from hydrogen, $C_1$–$C_8$ alkyl, aryl, $C_1$–$C_8$ alkaryl, $C_1$–$C_8$ alkoxy, aralkyl, and halo. Most preferred are compounds are those where the acid linker, —(L4)—, for $R_4$ is selected from the groups;

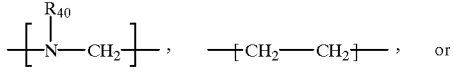

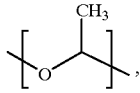

where $R_{40}$ is hydrogen or $C_1$–$C_8$ alkyl. Preferred as the (acidic group) in the group $R_4$ are acidic groups selected from:

-5-tetrazolyl,

—$SO_3H$,

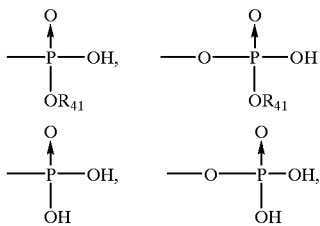

-continued

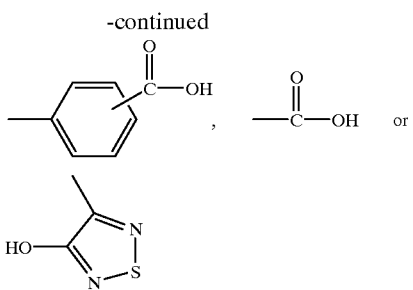

where $R_{41}$ is a metal or $C_1$–$C_8$ alkyl. A salt or prodrug derivative of the (acidic group) is also suitable.

Examples of salt derivatives of the (acidic group) $R_4$ are;

Examples of ester prodrug derivatives are of the (acidic group) $R_4$;

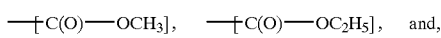

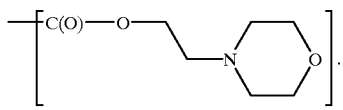

Particularly preferred are (acidic groups) selected from:

—$CO_2H$

—$SO_3H$

—$P(O)(OH)_2$ and salt, and prodrug (e.g., ester, amide) derivatives thereof.

The most preferred acidic group in the compounds of the invention is a carboxylic acid group, —$CO_2H$.

Preferred $R_5$ Substituents

A preferred subclass of compounds of formula (I) are those wherein all X's of group $R_5$ are oxygen.

Another preferred subclass of compounds of formula (I) are those wherein Z is a group selected from acetamide, glyoxylamide, or hydrazide, represented by the formulae (Va), (Vb), and (Vc);

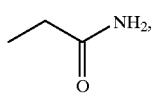
(Va)

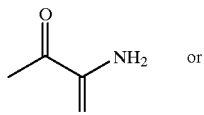
(Vb)

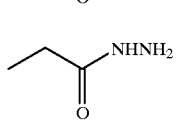
(Vc)

Most preferred are compounds of formula (I) wherein $R_5$ is the glyoxylamide group represented by the formula;

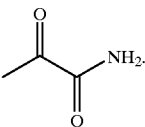

For the group $R_5$ it is preferred that linking group —($L_5$)— be a bond, particularly when the $R_5$ is a bond in combination with Z being the glyoxylamide group.

Preferred $R_6$ Substituents

Another preferred subclass of compounds of formula (I) are those wherein $R_6$ is selected from the group; hydrogen, methyl, ethyl, propyl, isopropyl, cyclopropyl, $C_1$–$C_3$ alkoxy, $C_1$–$C_3$ alkylthio, $C_1$–$C_3$ haloalkyl and halo.

Preferred $R_7$ Substituents

Another preferred subclass of compounds of formula (I) wherein the divalent linking group —($L_7$)— is selected from the formulae (VIIa), (VIIb), (VIIc), (VIId), (VIIe), and (VIIf):

(VIIa)

(VIIb)

(VIIc)

(VIId)

(VIIe)

(VIIf)

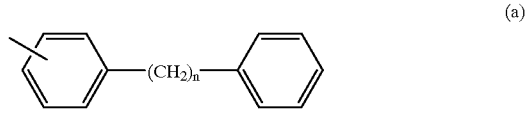

where $Q_2$ is a bond or any of the divalent groups (VIIa), (VIIb), (VIIc), (VIId), (VIIe), and (VIIf) and each $R_{70}$ is independently hydrogen, $C_{1-6}$ alkyl, $C_{1-6}$ haloalkyl or $C_{1-6}$ alkoxy.

Particularly preferred as the linking group —($L_7$)— of $R_7$ is an alkylene chain of 1 or 2 carbon atoms, namely, —($CH_2$)—, and —($CH_2$—$CH_2$)—.

The preferred group for $R_{71}$ is a substituted or unsubstituted group selected from the group consisting of $C_5$—$C_{14}$ cycloalkyl, $C_5$–$C_{14}$ cycloalkenyl, phenyl, naphthyl, norbornanyl, bicycloheptadienyl, toluoyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (a);

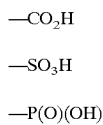
(a)

where n is a number from 1 to 8.

Substituents for $R_{71}$ are non-interfering radicals selected from halo, —$CF_3$, $C_1$–$C_{10}$ alkyl, $C_1$–$C_{10}$ alkoxy, —S—($C_1$–$C_{10}$ alkyl), and $C_1$–$C_{10}$ haloalkyl radicals. Particularly preferred are compounds wherein for $R_7$ the combined group —($L_7$)—$R_{71}$ is selected from the group consisting of

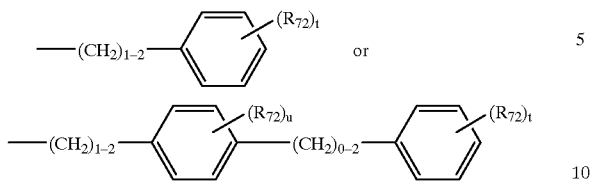

where $R_{72}$ is a radical independently selected from hydrogen, halo, —$CF_3$, $C_1$–$C_{10}$ alkyl, $C_1$–$C_{10}$ alkoxy, —S—($C_1$–$C_{10}$ alkyl), and $C_1$–$C_{10}$ haloalkyl, $C_1$–$C_{10}$ hydroxyalkyl and t is a number from 0 to 5 and u is a number from 0 to 4.

Preferred compounds of the invention are those having the general formula (II), or a pharmaceutically acceptable salt, solvate or prodrug derivative thereof;

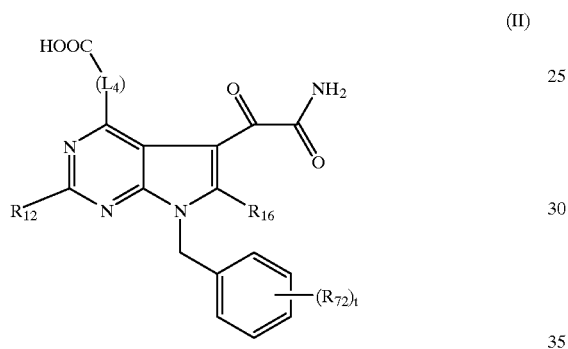

wherein;

$R_{12}$ is selected from hydrogen, halo, cyclopropyl, $C_1$–$C_8$ alkyl, $C_1$–$C_8$ alkoxy, $C_1$–$C_8$ alkylthio $C_1$–$C_8$ haloalkyl, $C_1$–$C_8$ hydroxyalkyl, phenyl, thiophenyl, thiomethyl, diethylamino, dimethylamino, and ethylamino.

—($L_4$)— is a divalent group selected from

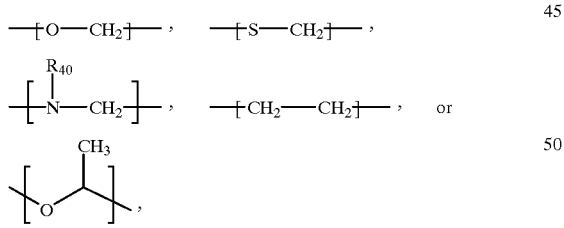

where $R_{40}$ is hydrogen $C_1$–$C_8$ alkyl.

$R_{16}$ is selected from hydrogen, methyl, ethyl, propyl, cyclopropyl, $C_1$–$C_3$ alkoxy, $C_1$–$C_3$ alkylthio, and $C_1$–$C_3$ haloalkyl.

$R_{72}$ is and $C_1$–$C_8$ alkyl, $C_1$–$C_8$ alkoxy, —S—($C_1$–$C_8$ alkyl), $C_1$–$C_8$ haloalkyl, $C_1$–$C_8$ hydroxyalkyl, —$CF_3$, and halo, phenyl, biphenyl, thiophenyl and t is an integer from 0 to 5. Preferred $R_{72}$ substituents are —Cl, —$CF_3$, and —F located at a position meta to the linking group attached to the nitrogen atom at the 7 position, for example, as shown in Formula IIa below;

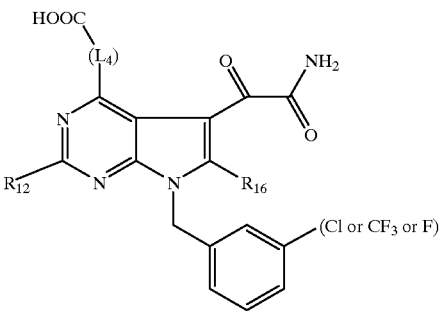

One set of specific preferred compounds and all pharmaceutically acceptable salts, solvates and prodrug derivatives thereof which are illustrative of the compounds of the invention include the following:

Compound 1

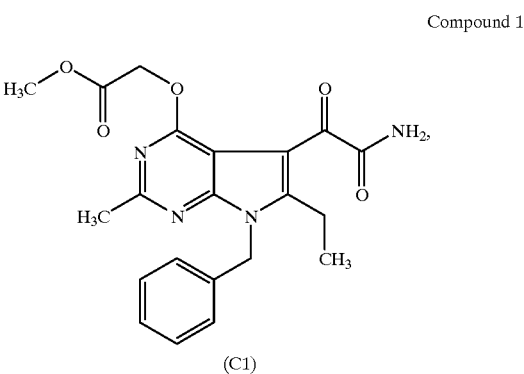

(C1)

Compound 2

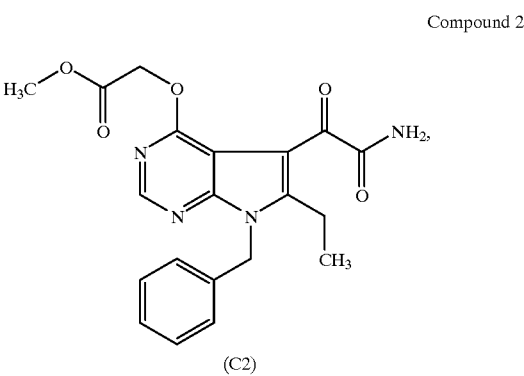

(C2)

Compound 3

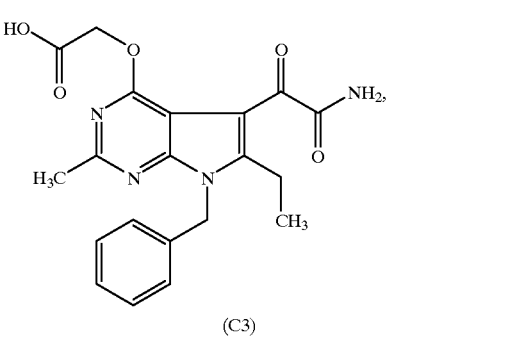

(C3)

-continued

Compound 4

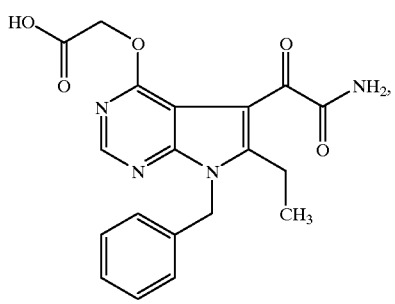

(C4)

and

Compound 5

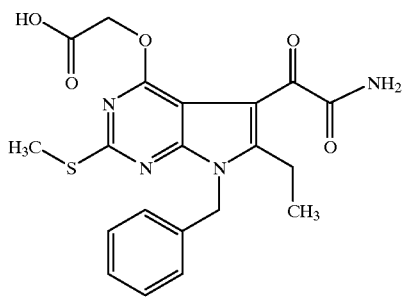

(C5)

Another set of specific preferred compounds and all pharmaceutically acceptable salts, solvates and prodrug derivatives thereof which are illustrative of the compounds of the invention include the following:

Y. [[2-(methylthio)-5-(aminooxoacetyl)-6-ethyl-7-(phenylmethyl)-7H-pyrrolo[2,3-d]pyrimidin-4-yl]oxy] acetic acid methyl ester, Z. [[2-(phenylthio)-5-(aminooxoacetyl)-6-ethyl -7-(phenylmethyl)-7H-pyrrolo[2,3-d]pyrimidin-4-yl]oxy] acetic acid methyl ester, AA. [[2-(phenylthio)-5-(aminooxoacetyl)-6-ethyl-7-(phenylmethyl)-7H-pyrrolo[2,3-d]pyrimidin-4-yl]oxy] acetic acid, AB. [[2-methoxy-5-(aminooxoacetyl)-6-ethyl-7-(phenylmethyl)-7H-pyrrolo[2,3-d]pyrimidin-4-yl]oxy] acetic acid methyl ester, AC. [[2-methoxy-5-(aminooxoacetyl)-6-ethyl-7-(phenylmethyl)-7H-pyrrolo[2,3-d]pyrimidin-4-yl]oxy] acetic acid, AF. [[5-(aminooxoacetyl)-6-ethyl-7-([1,1'-biphenyl]-2-ylmethyl)-7H-pyrrolo[2,3-d]pyrimidin-4-yl]oxy]acetic acid methyl ester, AG. [[5-(aminooxoacetyl)-6-ethyl-7-([1,1'-biphenyl]-2-ylmethyl)-7H-pyrrolo[2,3-d]pyrimidin-4-yl]oxy]acetic acid, AK. [[5-(aminooxoacetyl)-6-ethyl-7-[(3-fluorophenyl) methyl]-7H-pyrrolo[2,3-d]pyrimidin-4-yl]oxy]acetic acid methyl ester, AL. [[5-(aminooxoacetyl)-6-ethyl-7-[(3-fluorophenyl) methyl]-7H-pyrrolo[2,3-d]pyrimidin-4-yl]oxy]acetic acid, AN. [[2-(methylthio)-5-(aminooxoacetyl)-6-ethyl-7-([1,1'-biphenyl]-2-ylmethyl)-7H-pyrrolo[2,3-d]pyrimidin-4-yl] oxy]acetic acid methyl ester, AO. [[2-(methylthio)-5-(aminooxoacetyl)-6-ethyl-7-([1,1'-biphenyl]-2-ylmethyl)-7H-pyrrolo[2,3-d]pyrimidin-4-yl] oxy]acetic acid, AP. [[2-(methylthio)-5-(aminooxoacetyl)-6-ethyl-7-[(3-fluorophenyl)methyl]-7H-pyrrolo[2,3-d]pyrimidin-4-yl] oxy]acetic acid methyl ester, AQ. [[2-(methylthio)-5-(aminooxoacetyl)-6-ethyl-7-[(3-fluorophenyl)methyl]-7H-pyrrolo[2,3-d]pyrimidin-4-yl] oxy]acetic acid, AR. [[2-(methylthio)-5-(aminooxoacetyl)-6-ethyl-7-[[3-(trifluoromethyl)phenyl]methyl]-7H-pyrrolo[2,3-d] pyrimidin-4-yl]oxy]acetic acid methyl ester, AS. [[2-(methylthio)-5-(aminooxoacetyl)-6-ethyl-7-[[3-(trifluoromethyl)phenyl]methyl]-7H-pyrrolo[2,3-d] pyrimidin-4-yl]oxy]acetic acid, AT. [[2-(methylthio)-5-(aminooxoacetyl)-6-ethyl-7-[(3-chlorophenyl)methyl]-7H-pyrrolo[2,3-d]pyrimidin-4-yl] oxy]acetic acid methyl ester, AU. [[2-(methylthio)-5-(aminooxoacetyl)-6-ethyl-7-[(3-chlorophenyl)methyl]-7H-pyrrolo[2,3-d]pyrimidin-4-yl] oxy]acetic acid, AY. [[5-(aminooxoacetyl)-6-ethyl-7-[(3-chlorophenyl) methyl]-7H-pyrrolo[2,3-d]pyrimidin-4-yl]oxy]acetic acid methyl ester, AZ. [[5-(aminooxoacetyl)-6-ethyl-7-[(3-chlorophenyl) methyl]-7H-pyrrolo[2,3-d]pyrimidin-4-yl]oxy]acetic acid, BD. [[5-(aminooxoacetyl)-6-ethyl-7-[[3-trifluoromethyl) phenyl]methyl]-7H-pyrrolo[2,3-d]pyrimidin-4-yl]oxy] acetic acid methyl ester, BE. [[5-(aminooxoacetyl)-6-ethyl-7-[[3-(trifluoromethyl) phenyl]methyl]-7H-pyrrolo[2,3-d]pyrimidin-4-yl]oxy] acetic acid, BDA.[[2-(methylthio)-5-(aminooxoacetyl)-6-ethyl-7-[[2-(trifluoromethyl)phenyl]methyl]-7H-pyrrolo[2,3-d] pyrimidin-4-yl]oxy]acetic acid methyl ester, and BDB. [[2-(methylthio)-5-(aminooxoacetyl)-6-ethyl-7-[[2-(trifluoromethyl)phenyl]methyl]-7H-pyrrolo[2,3-d] pyrimidin-4-yl]oxy]acetic acid.

The salts of the above pyrrolo[2,3-d]pyrimidine compounds represented by formulae (I) and (II) are an additional aspect of the invention. In those instances where the compounds of the invention possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin. For example, the (acidic group) of the substituent $R_4$ of Formula I may be selected as —$CO_2H$ and salts may be formed by reaction with appropriate bases (e.g., NaOH, KOH) to yield the corresponding sodium and potassium salt.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain compounds of the invention may possess one or more chiral centers and may thus exist in optically active forms. Likewise, when the compounds contain an alkenyl or alkenylene group there exists the possibility of cis- and trans-isomeric forms of the compounds. The R- and S-isomers and mixtures thereof, including racemic mixtures as well as mixtures of cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound. This changes the racemic form into a mixture of diastereomers and diastereomers, because they have different melting points, different boiling points, and different solubilities can be separated by conventional means, such as crystallization.

Prodrugs are derivatives of the compounds of the invention which have chemically or metabolically cleavable groups and become by solvolysis or under physiological conditions the compounds of the invention which are pharmaceutically active in vivo. Derivatives of the compounds of this invention have activity in both their acid and base derivative forms, but the acid derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters derived from acidic groups pendent on the compounds of this invention are preferred prodrugs. In some cases it is desirable to prepare double ester type prodrugs such as (acyloxy)alkyl esters or ((alkoxycarbonyl)oxy)alkyl esters. Particularly preferred esters as prodrugs are methyl, ethyl, propyl, isopropyl, n-butyl, isobutyl, tert-butyl, morpholinoethyl, and N,N-diethylglycolamido.

N,N-diethylglycolamido ester prodrugs may be prepared by reaction of the sodium salt of a compound of Formula (I) (in a medium such as dimethylformamide) with 2-chloro-N,N-diethylacetamide (available from Aldrich Chemical Co., Milwaukee, Wis. USA; Item No. 25,099-6).

Morpholinylethyl ester prodrugs may be prepared by reaction of the sodium salt of a compound of Formula (I) (in a medium such as dimethylformamide) with 4-(2-chloroethyl)morpholine hydrochloride (available from Aldrich Chemical Co., Milwaukee, Wis. USA, Item No. C4,220-3).

Method of Making the Compounds of the Invention

The synthesis of the pyrrolo[2,3-d]pyrimidines of the invention (viz., Compounds of Formula I) can be accomplished by well known methods as recorded in the chemical literature. Those procedures useful for the syntheses of the compounds of the invention are illustrated herein and outlined in the following reaction Scheme 1

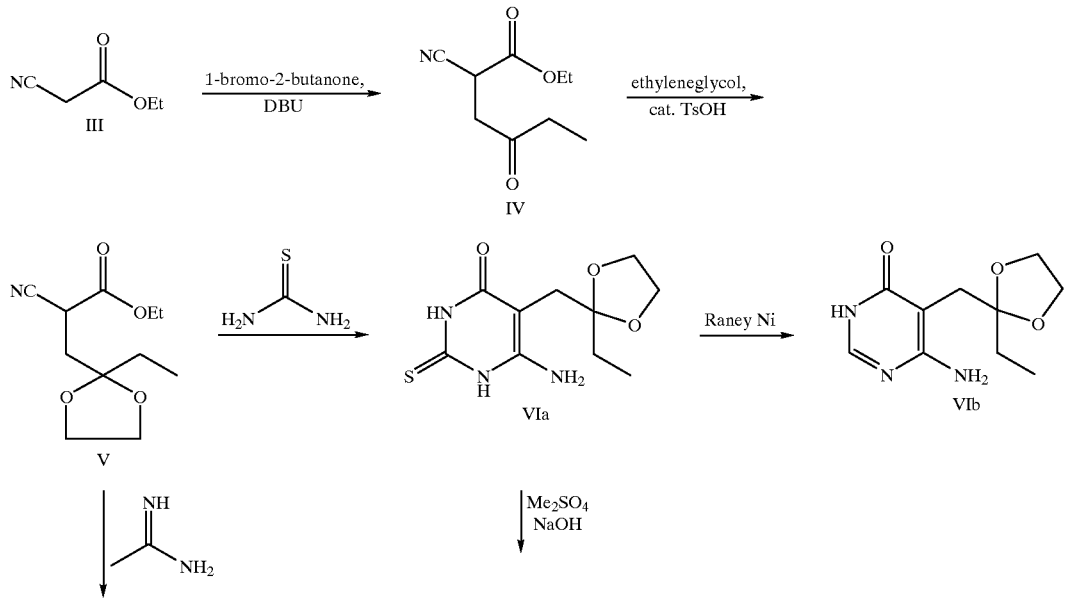

-continued
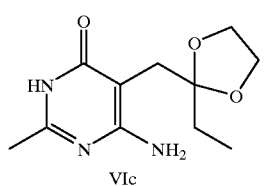
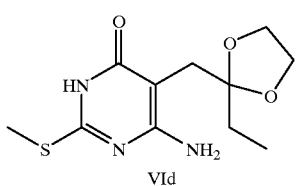
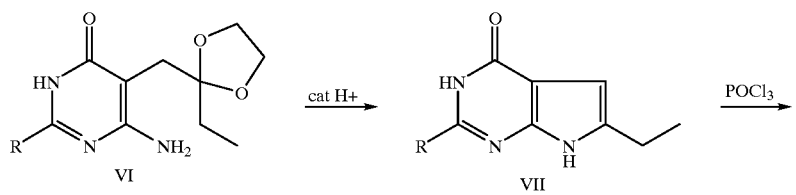
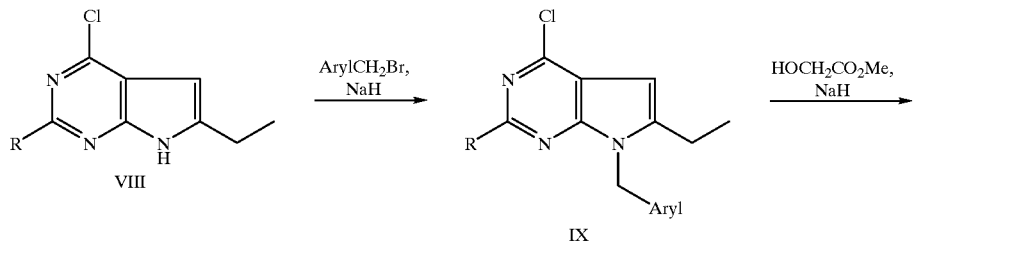
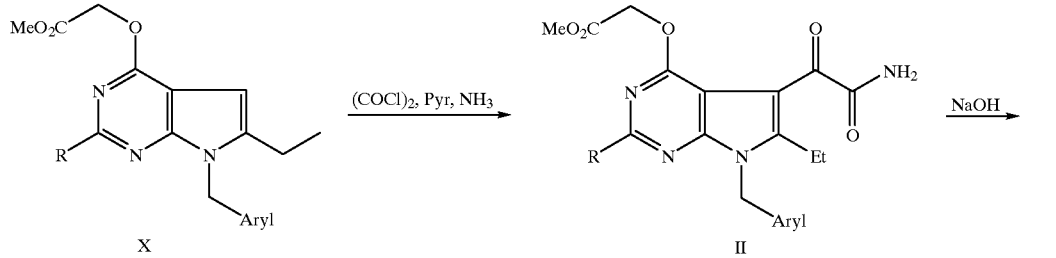
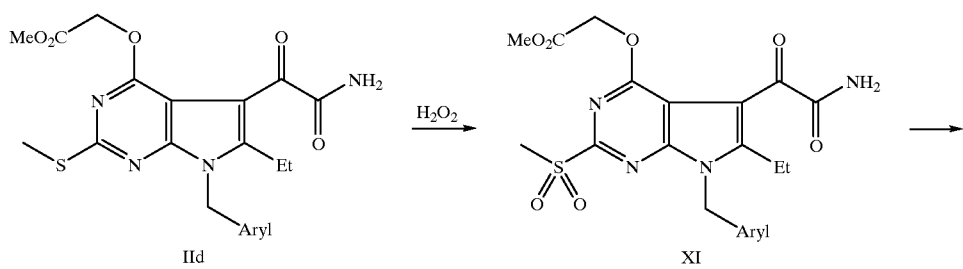

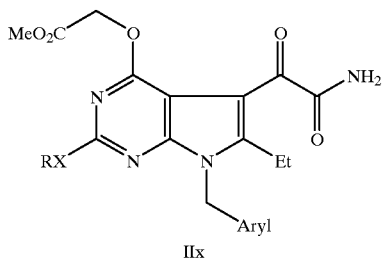

IIx

RX = Cl, RS, CN, RO, R₂N

Ethylcyano acetate compound III was alkylated with 1-bromo-2-butanone to provide compound IV. The ethyl group of the ketone eventually becomes the ethyl substituent at the 6 position of the pyrrolopyrimidine. The ketone is treated with an alcohol under mildly acidic conditions generating a ketal, compound V. Compound V can then be reacted under basic to neutral conditions with ureas, thioureas, and amidines. For example, compound V can be reacted with thiourea under basic conditions to provide compound VIa, 2-thiopyrimidone. The thio group can be hydrogenolized using Raney Nickel to provide the 2-unsubstituted pyrimidone. Likewise, compound V can be reacted under neutral conditions with acetamidine to provide the 2-methylpyrimidone, compound VIc. Compound VI can be cyclized to a pyrrolopyrimidine compound VII, and reacted with POCl₃ to produce the 2-substituted 4-chloropyrrolpyrimidine, compound VIII. The nitrogen at the 7 position is then alkylated under basic conditions and the chloride displaced with enough glycolate to provide compound X. The glyoxamide side chain was incorporated using an excess of oxalyl chloride in the presence of pyridine followed by quench with ammonia. This provides the compound of the invention, (C2), supra. Straightforward hydrolysis of the methyl ester followed by acidification provides compound I (C4) supra. The sulfur group can be oxidized and displaced with a variety of nucleophiles which is described at the bottom as going from compound IId, to compound XI, to compound IIx.

Methods of Using the Compounds of the Invention

Pyrrolo[2,3-d]pyrimidines described herein are believed to achieve their beneficial therapeutic action principally by direct inhibition of mammalian (including human) sPLA₂, and not by acting as antagonists for arachidonic acid, nor other active agents below arachidonic acid in the arachidonic acid cascade, such as 5-lipoxygenases, cyclooxygenases, and etc.

The method of the invention for inhibiting sPLA₂ mediated release of fatty acids comprises contacting mammalian sPLA₂ with an therapeutically effective amount of pyrrolo [2,3-d]pyrimidines corresponding to Formulae (I) or (II) as described herein including salt or a prodrug derivative thereof.

Another aspect of this invention is a method for treating Inflammatory Diseases such as inflammatory bowel disease, septic shock, adult respiratory distress syndrome, pancreatitis, trauma, bronchial asthma, allergic rhinitis, rheumatoid arthritis, osteoarthritis, and related diseases which comprises administering to a mammal (including a human) a therapeutically effective dose pyrrolo[2,3-d] pyrimidines of the invention (see, formulae I and II).

As previously noted the compounds of this invention are useful for inhibiting sPLA₂ mediated release of fatty acids such as arachidonic acid. By the term, "inhibiting" is meant the prevention or therapeutically significant reduction in release of sPLA₂ initiated fatty acids by the compounds of the invention. By "pharmaceutically acceptable" it is meant the carrier, diluent or excipient must be compatible with the other ingredients of the formulation and not deleterious to the recipient thereof.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

Preferably compounds of the invention (per Formulae I or II) or pharmaceutical formulations containing these compounds are in unit dosage form for administration to a mammal. The unit dosage form can be a capsule or tablet itself, or the appropriate number of any of these. The quantity of Active ingredient in a unit dose of composition may be varied or adjusted from about 0.1 to about 1000 milligrams or more according to the particular treatment involved. It may be appreciated that it may be necessary to make routine variations to the dosage depending on the age and condition of the patient. The dosage will also depend on the route of administration.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the pyrrolo[2,3-d]pyrimidines of the invention together with a pharmaceutically acceptable carrier or diluent therefor. The present pharmaceutical formulations are prepared by known procedures using well known and readily available ingredients.

In making the compositions of the present invention, the Active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. For example, for intravenous injection the compounds of the invention may be dissolved in at a concentration of 2 mg/ml in a 4% dextrose/0.5% Na citrate aqueous solution. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders the carrier is a finely divided solid which is in admixture with the finely divided Active ingredient. In tablets the Active ingredient is mixed with a carrier having the necessary binding properties in suitable proportions and compacted in the shape and size desired. The powders and tablets preferably contain from about 1 to about 99 weight percent of the Active ingredient which is the novel compound of this invention. Suitable solid carriers are magnesium carbonate, magnesium stearate, talc, sugar lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs.

The Active ingredient can be dissolved or suspended in a pharmaceutically acceptable carrier, such as sterile water, sterile organic solvent or a mixture of both. The Active ingredient can often be dissolved in a suitable organic solvent, for instance aqueous propylene glycol. Other compositions can be made by dispersing the finely divided Active ingredient in aqueous starch or sodium carboxymethyl cellulose solution or in a suitable oil.

The following pharmaceutical formulations 1 thru 8 are illustrative only and are not intended to limit the scope of the invention in any way. "Active ingredient", refers to a compound according to Formula (I) or (II) or a pharmaceutically acceptable salt, solvate, or prodrug thereof.

FORMULATION 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

FORMULATION 2

|  | Quantity (mg/tablet) |
| --- | --- |
| Active ingredient | 250 |
| Cellulose, microcrystalline | 400 |

-continued

|  | Quantity (mg/tablet) |
| --- | --- |
| Silicon dioxide, fumed | 10 |
| Stearic acid | 5 |
| Total | 665 mg |

The components are blended and compressed to form tablets each weighing 665 mg

FORMULATION 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

FORMULATION 4

Tablets, each containing 60 mg of Active ingredient, are made as follows:

|  |  |
| --- | --- |
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The Active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules, each containing 80 mg of Active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The Active ingredient, cellulose, starch, and magnesium stearate are blended, passed through a No. 45 mesh U.S. sieve, and filled into hard gelatin capsules in 200 mg quantities.

FORMULATION 6

Suppositories, each containing 225 mg of Active ingredient, are made as follows:

| Active ingredient | 225 mg |
|---|---|
| Saturated fatty acid glycerides | 2,000 mg |
| Total | 2,225 mg |

The Active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions, each containing 50 mg of Active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The Active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 8

An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

All of the products of the Examples described below as well as intermediates used in the following procedures showed satisfactory nmr and ir spectra. They also had the correct mass spectral values.

EXAMPLE 1

This example illustrates the preparation of five pyrrolo[2,3-d]pyrimidine compounds having utility as sPLA$_2$ inhibitors. These compounds are represented by the following structural formulae:

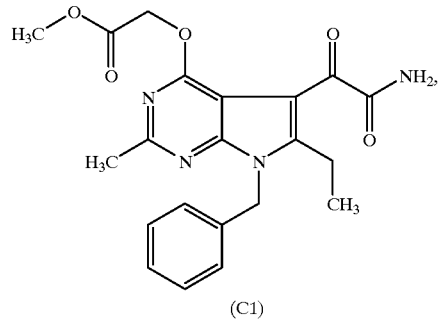

(C1)

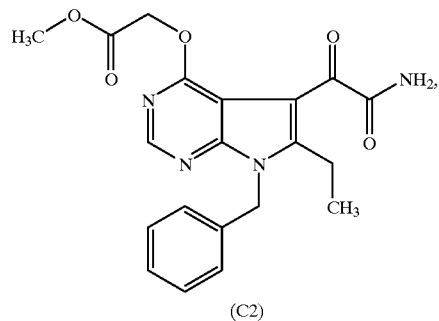

(C2)

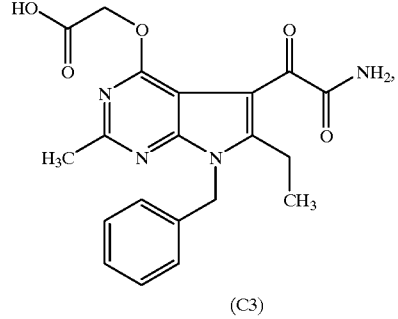

(C3)

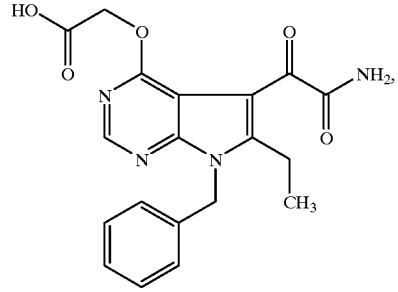

(C4)

and

Compound 5

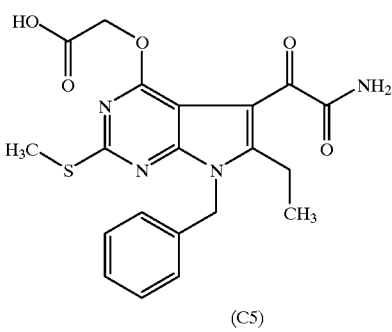

(C5)

A. Preparation of 2-cyano-4-oxohexanoic Acid Ethyl Ester

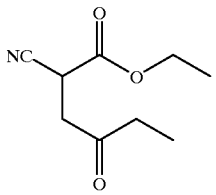

To a 5° C. solution containing 27.8 g (246 mmol) of ethyl cyanoacetate and 38.2 g (251 mmol) of 1,8-diazabicyclo[5.4.0]undec-7ene in 420 mL of benzene was added over 30 minutes a solution of 1-bromo-2-butanone in 70 mL of benzene. The ice bath was removed and the reaction stirred for 1 hour at ambient temperature. At this time, the solids were removed by filtration and washed with 100 mL of methyl tert-butyl ether. The filtrate and the wash were combined and concentrated. The crude product was purified by short path distillation (0.2 torr, 140° C.) to provide 40.0 g (88.9%) of 2-cyano-4-oxohexanoic acid ethyl ester as a colorless oil. nmr (500 MHz, CDCl$_3$) δ1.09 (t, J=7.3 Hz, 3H), 1.31 (t, J=7.1 Hz, 3H), 2.50 (q, J=7.3 Hz, 2H), 2.96 (dd, J=5.5, 18.0 Hz, 1H), 3.16 (dd, J=7.2, 18.0 Hz, 1H), 3.96 (dd, J=5.5, 7.2 Hz, 1H), 4.25 (q, J=7.1 Hz, 2H).

B. Preparation of α-cyano-2-ethyl-1,3-dioxolane-2-propanoic Acid Ethyl Ester

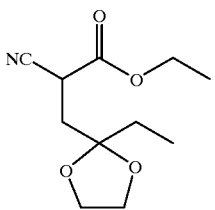

In a 500 mL flask equipped with a reflux condenser and Dean-Stark trap were combined 40.0 g (218 mmol) of 2-cyano-4-oxohexanoic acid ethyl ester, 20.3 g (327 mmol) of ethylene glycol, 0.83 g (4.3 mmol) of p-toluenesulfonic acid monohydrate, and 100 mL of benzene. The reaction was heated to reflux until approximately 4.5 mL of water had been collected in the trap. The reaction was cooled to ambient temperature, washed with 50 mL of water, 50 mL of saturated δsodium bicarbonate solution and dried over sodium sulfate. The mixture was then concentrated to 46.0 g (93%) of α-cyano-2-ethyl-1,3-dioxolane-2-propanoic acid ethyl ester as a light tan oil. An NMR of the crude product showed less than 10% residual ketone remained and the crude product was used without further purification. nmr (500 MHz, CDCl$_3$) δ0.92 (t, J=7.5 Hz, 3H), 1.31 (t, J=7.2 Hz, 3H), 1.64 (q, J=7.5 Hz, 2H), 2.29 (dd, J=6.8, 14.6 Hz, 1H), 2.41 (dd, J=6.3, 14.6 Hz, 1H), 3.59 (dd, J=6.3, 6.8 Hz, 1H), 3.59 (m, 4H), 4.24 (q, J=7.2 Hz, 2H).

C. Preparation of the compound 6-amino-5-(2-methyl-1,3-dioxolan-2-ylmethyl)-2-thiouracil, a Compound Represented by the Formula

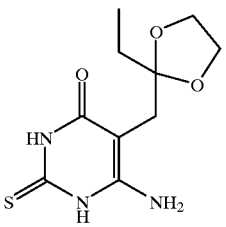

To a 60° C. solution of sodium ethoxide, prepared from 1.92 g (80 mmol) of sodium hydride and 60 of ethanol, was added 6.09 g (80 mmol) of thiourea and 18.2 g (80mmol) of α-cyano-2-ethyl-1,3-dioxolane-2-propanoic acid ethyl ester. The mixture was heated to 75° C. for 4 hours then allowed to cool to ambient temperature and stirred for 18 hours. The reaction was then concentrated to a solid. The solid was dissolved in 100 mL of water and the solution adjusted to pH 6.9 with glacial acetic acid which caused a solid to precipitate. The solid was collected by filtration and washed with 100 mL of water. The wet cake was combined with 60 mL of ethanol and stirred for 15 minutes. The remaining solids were collected by filtration, washed with 40 mL of ethanol, and dried in vacuo (40° C., 10 torr) to provide 11.0 g (53.4%) of 6-amino-5-(2-ethyl-1,3-dioxolan-2-ylmethyl)-2-thiouracil as a cream colored solid. nmr (500 MHz, dmso-d$_6$) δ0.80 (t, J=7.4 Hz, 3H), 1.51 (q, J=7.4 Hz, 2 H), 2.51 (s, 2H), 3.81 (m, 2H), 3.92 (m, 2H), 5.95 (s, 2H), 11.43 (s, 1H), 11.69 (s, 1H)

D. Preparation of the Compound 6-amino-5-(2-ethyl-1,3-dioxolan-2-ylmethyl)-4-pyrimidinol

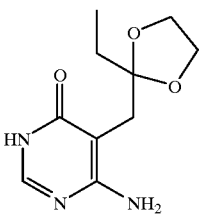

A mixture of 7.72 g (30 mmol) of 6-amino-5-(2-ethyl-1,3-dioxolan-2-ylmethyl)-2-thiouracil, 22.5 g of Raney Ni, 330 mL of water, and 23 mL of concentrated ammonium hydroxide was heated to reflux for 150 minutes. The mixture was filtered warm and then concentrated under vacuum to 6.34 g of tan solid. The solid was slurried in 100 mL of ethyl ether and solids collected by filtration. The solids were dried to 6.16 g (91.2%) of 6-amino-5-(2-ethyl-1,3-dioxolan-2-ylmethyl)-4-pyrimidinol as an off white solid. nmr (500 MHz, dmso-d$_6$) δ0.82 (t, J=7.4 Hz, 3H), 1.54 (q, J=7.4 Hz, 2H), 2.63 (s, 2H), 3.85 (m, 2H), 3.95 (m, 2H), 6.10 (s, 2H), 7.71 (s, 1H), 11.45 (s, 1H)

E. Preparation of 2-methyl-6-amino-5-(2-ethyl-1,3-dioxolan-2-ylmethyl)-4-pyrimidinol

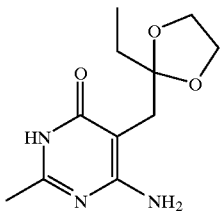

A solution of sodium ethoxide (prepared from 0.96 g (40 mmol) of sodium hydride and 40 mL of ethanol) was treated with 3.78 g (40 mmol) of acetamidine hydrochloride and 9.09 g (40 mmol) of a-cyano-2-ethyl-1,3-dioxolane-2-propanoic acid ethyl ester. The mixture was heated to reflux for 150 minutes, cooled to ambient temperature and concentrated under vacuum. The solid residue was dissolved in 50 mL of water and the resulting solution washed with ethyl ether. The product precipitated upon neutralization to pH 7.0 with glacial acetic acid. The precipitate was collected by filtration, washed with water, and dried to 0.70 g (7.5%) of 2-methyl-6-amino-5-(2-ethyl-1,3-dioxolan-2-ylmethyl)-4-pyrimidinol. The filtrate and wash were combined and concentrated. The resulting solid was slurried in ethyl ether and solids collected to provide an additional 1.3 g (14%) of 2-methyl-6-amino-5-(2-ethyl-1,3-dioxolan-2-ylmethyl)-4-pyrimidinol as a tan solid. nmr (500 MHz, dmso-d$_6$) δ0.79 (t, J=7.4 Hz, 3H), 1.51 (q, J=7.4 Hz, 2H), 2.10 (s, 3H), 2.58 (s, 2H), 3.83 (m, 2H), 3.93 (m, 2H), 6.00 (s, 2H), 11.38 (s, 1H)

F. Preparation of 2-(methylthio)-6-amino-5-(2-ethyl-1,3-dioxolan-2-ylmethyl)-4-pyrimidinol

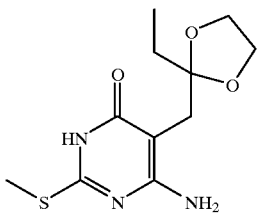

To a slurry of 3.95 g (15.3 mmol) of 6-amino-5-(2-ethyl-1,3-dioxolan-2-ylmethyl)-2-thiouracil, 27 mL of ethanol, 3 mL of water and 3.06 mL of 5 M sodium hydroxide was added 1.93 g (15.3 mmol) of methyl sulfate. The reaction exothermed to 45° C. and became a solution. After stirring for 6 hours at ambient temperature, the precipitate was collected by filtration. The solids were washed with 15 mL of water and dried in vacuo (40° C., 10 torr) to yield 2.78 g (67%) of 2-(methylthio)-6-amino-5-(2-ethyl-1,3-dioxolan-2ylmethyl)-4-pyrimidinol as a white powder. nmr (500 MHz, dmso-d$_6$) δ0.80 (t, J=7.4 Hz, 3H), 1.52 (q, J=7.4 Hz, 2H), 2.42 (s, 3H), 2.58 (s, 2H), 3.82 (m, 2H), 3.92 (m, 2H), 6.10 (s, 2H), 11.6 (bs, 1H)

G. Preparation of 1,7-dihydro-6-ethyl-2-(methylthio)-4H-pyrrolo[2,3-d]pyrimidin-4-one

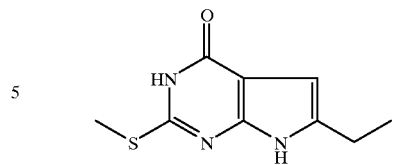

The 2-(methylthio)-6-amino-5-(2-ethyl-1,3-dioxolan-2ylmethyl)-4-pyrimidinol (2.50 g, 9.21 mmol) was combined with 69 mL of 0.2 M HCl and stirred at ambient temperature for 18 hours. The solids were collected by filtration, washed with 20 mL of water and dried in vacuo (40° C., 10 torr) to provide a quantitative yield of 1,7-dihydro-6-ethyl-2-(methylthio)-4H-pyrrolo[2,3-d]pyrimidin-4-one as a white solid. nmr (500 MHz, dmso-d$_6$) δ1.17 (t, J=7.5 Hz, 3H), 2.49 (s, 3H), 2.55 (q, J=7.5 Hz, 2H), 6.03 (s, 1H), 11.61 (s, 1H), 11.95 (s, 1H)

H. Preparation of 1,7-dihydro-6-ethyl-4H-pyrrolo[2,3-d]pyrimidin-4-one

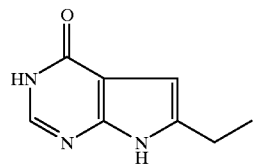

The 6-amino—S—(2-ethyl-1,3-dioxolan-2-ylmethyl)-4-pyrimidinol (6.00 g, 26.6 mmol) was combined with 200 mL of 0.2 M HCl and stirred at ambient temperature for 18 hours. The solids were collected by filtration, washed with 40 mL of water and dried in vacuo (40° C., 10 torr) to 3.50 g (81%) of 1,7-dihydro-6-ethyl-4H-pyrrolo[2,3-d]pyrimidin-4-one as a white solid. nmr (500 MHz, dmso-d$_6$) δ1.21 (t, J=7.5 Hz, 3H), 2.62 (q, J=7.5 Hz, 2H), 6.14 (s, 1H), 7.76 (s, 1H), 11.67 (bs, 2H)

I. Preparation of 1,7-dihydro-2-methyl-6-ethyl-4H-pyrrolo[2,3-d]pyrimidin-4-one

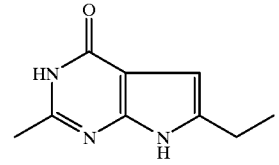

The 2-methyl-6-amino-5-(2-ethyl-1,3-dioxolan-2-ylmethyl)-4-pyrimidinol (5.50 g, 22.9 mmol) was combined with 172 mL of 0.2 M HCl and stirred at ambient temperature for 18 hours. The solids were collected by filtration, washed with 40 mL of water and dried in vacuo (40° C., 10 torr) to 3.70 g (91%) of 1,7-dihydro-2-methyl-6-ethyl-4H-pyrrolo[2,3-d]pyrimidin-4-one as a tan solid. nmr (500 MHz, dmso-d$_6$) δ1.18 (t, J=7.5 Hz, 3H), 2.26 (s, 3H), 2.57 (q, J=7.5 Hz, 2H), 6.04 (s, 1H), 11.42 (s, 1H), 11.57 (s, 1H)

J. Preparation of 2-(methylthio)-4-chloro-6-ethyl-1H-pyrrolo[2,3-d]pyrimidine

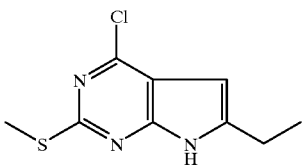

Phosphorous oxychloride (21 mL) was carefully added to a mixture of 5.66 g (27.0 mmol) of 1,7-dihydro-6-ethyl-2-(methylthio)-4H-pyrrolo[2,3-d]pyrimidin-4-one and 1.70 mL of N,N-dimethylaniline. The reaction was heated to 95° C. for 12 hours. At this time the reaction was cooled and concentrated under vacuum. The residue was combined with 60 g of ice and stirred for 1 hour. The solids were collected by filtration, washed with 30 mL of water and suspended in 100 mL of water. The solids were again collected, washed with 30 mL of water, and dried in vacuo (40° C., 10 torr) to provide 5.50 g (89.6%) of 2-(methylthio)-4-chloro-6-ethyl-1H-pyrrolo[2,3-d]pyrimidine as a yellow solid. nmr (500 MHz, dmso-$d_6$) δ1.24 (t, J=7.5 Hz, 3H), 2.52 (s, 3H), 2.70 (q, J=7.5 Hz, 2H), 6.21 (s, 1H), 12.27 (s, 1H)

K. Preparation of 4-chloro-6-ethyl-1H-pyrrolo[2,3-d]pyrimidine

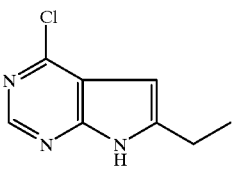

A solution of 3.35 g (20.5 mmol) of 1,7-dihydro-6-ethyl-4H-pyrrolo[2,3-d]pyrimidin-4-one in 187 mL of phosphorous oxychloride was heated to reflux for 4 hours. The reaction was cooled to ambient temperature and concentrated under vacuum. The residue was dissolved in 100 mL of methylene chloride and poured onto 100 g of ice. The mixture was neutralized to pH 7 by the addition of powdered potassium carbonate. After an additional 200 mL of methylene chloride and 200 mL of water were added, some solids remained and were removed by filtration. The solids were shown to be desired product by thin layer chromatography (silica, 19:1 methylene chloride-methanol). The solids were combined with the organic phase and concentrated to 4.0 g of brown residue. The residue was purified by flash chromatography (200 g of silica, 19:1 methylene chloride-methanol) to provide 2.50 g (67%) of 4-chloro-6-ethyl-1H-pyrrolo[2,3-d]pyrimidine as a white solid. nmr (500 MHz, dmso-$d_6$) δ1.27 (t, J=7.5 Hz, 3H), 2.76 (q, J=7.5 Hz, 2H), 6.30 (s, 1H), 8.48 (s, 1H), 12.41 (s, 1H)

L. Preparation of 2-methyl-4-chloro-6-ethyl-1H-pyrrolo[2,3-d]pyrimidine

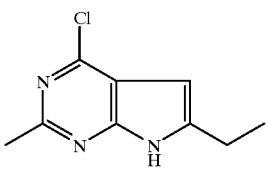

A solution of 3.50 g (19.8 mmol) of 1,7-dihydro-2-methyl-6-ethyl-4H-pyrrolo[2,3-d]pyrimidin-4-one in 180 mL of phosphorous oxychloride was heated to reflux for 4 hours. The reaction was cooled to ambient temperature and concentrated under vacuum. The residue was dissolved in 100 mL of methylene chloride and poured onto 100 g of ice. The mixture was neutralized to pH 7 by the addition of powdered potassium carbonate. After an additional 200 mL of methylene chloride and 200 mL of water were added, some solids remained and were removed by filtration. The solids were shown to be desired product by thin layer chromatography (silica, 19:1 methylene chloride-methanol). The solids were combined with the organic phase and concentrated to 4.0 g of brown residue. The residue was purified by flash chromatography (200 g of silica, 19:1 methylene chloride-methanol) to provide 3.32 g (86%) of 2-methyl-4-chloro-6-ethyl-1H-pyrrolo[2,3-d]pyrimidine as an off-white solid. nmr (500 MHz, dmso-$d_6$) δ1.25 (t, J=7.5 Hz, 3H), 2.56 (s, 3H), 2.73 (q, J=-7.5 Hz, 2H), 6.21 (s, 1H), 12.15 (s, 1H)

M. Preparation of 2-(methylthio)-4-chloro-6-ethyl-7-(phenylmethyl)-7H-pyrrolo[2,3-d]pyrimidine

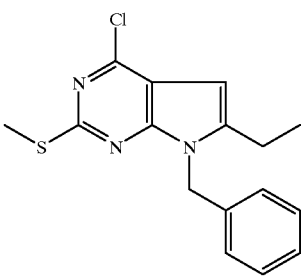

A solution of 5.30 g (23.2 mmol) of 2-(methylthio)-4-chloro-6-ethyl-1H-pyrrolo[2,3-d]pyrimidine in 160 mL of tetrahydrofuran (THF) was added to a 0° C. slurry of 7.96 g (46.5 mmol) of benzylbromide and 1.12 g (46.5 mmol) of sodium hydride in 40 mL of THF. The reaction was allowed to warm to ambient temperature and stirred for 18 hours. The reaction was quenched by the addition of 70 mL of brine. The organic phase was dried with sodium sulfate and concentrated to 12.0 g of brown oil. The oil was purified by flash chromatography using 1 Kg of silica gel and methylene chloride as an eluent to provide 6.40 g (87%) of 2-(methylthio)-4-chloro-6-ethyl-7-(phenylmethyl)-7H-pyrrolo[2,3-d]pyrimidine as a light yellow solid. nmr (500 MHz, CDCl$_3$) δ1.29 (t, J=7.5 Hz, 3H), 2.60 (s, 3H), 2.61 (q, J=7.5 Hz, 2H), 5.41 (s, 2H), 6.28 (s, 1H), 7.07 (d, J=6.8 Hz, 2H), 7.28 (m, 3H)

N. Preparation of 4-chloro-6-ethyl-7-(phenylmethyl)-7H-pyrrolo[2,3-d]pyrimidine

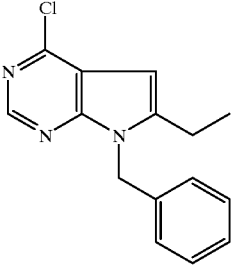

A solution of 2.35 g (12.9 mmol) of 4-chloro-6-ethyl-1H-pyrrolo[2,3-d]pyrimidine in 60 mL of tetrahydrofuran (THF) was added to a 0° C. slurry of 2.20 g (12.9 mmol) of benzylbromide and 0.31 g (12.9 mmol) of sodium hydride in 20 mL of THF. The reaction was allowed to warm to ambient temperature and stirred for 18 hours. The reaction was quenched by the addition of 20 mL of 2 M sodium hydrogen sulfate and then extracted with 70 mL of ethyl acetate. The organic phase was dried with sodium sulfate and concentrated to 4.0 g of off-white solid. The solid was purified by flash chromatography using (100 g of silica gel, methylene chloride) to provide 1.53 g (43%) of 4-chloro-6-ethyl-7-(phenylmethyl)-7H-pyrrolo[2,3-d]pyrimidine as a white solid. nmr (500 MHz, CDCl$_3$) δ1.32 (t, J=7.4 Hz, 3H), 2.67 (q, J=7.4 Hz, 2H), 5.49 (s, 2H), 6.40 (s, 1H), 7.04 (d, J=7.0 Hz, 2H), 7.28 (m, 3H), 8.60 (s, 1H)

O. Preparation of 2-methyl-4-chloro-6-ethyl-7-(phenylmethyl)-7H-pyrrolo[2,3-d]pyrimidine

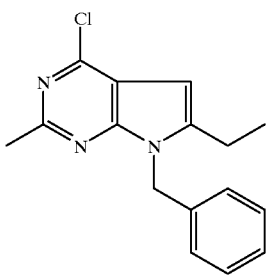

A solution of 500 mg (2.55 mmol) of 2-methyl-4-chloro-6-ethyl-1H-pyrrolo[2,3-d]pyrimidine in 5.0 mL of tetrahydrofuran (THF) was added to a 2° C. slurry of 437 mg (2.55 mmol) of benzylbromide and 60 mg (2.55 mmol) of sodium hydride in 4.0 mL of THF. The reaction was allowed to warm to ambient temperature and stirred for 18 hours. The reaction was quenched by the addition of 7 mL of 2 M sodium hydrogen sulfate and then extracted with 7 mL of ethyl acetate. The organic phase was dried with sodium sulfate and concentrated to 500 mg. The residue was purified by flash chromatography (50 g of silica gel, methylene chloride) to provide 490 mg (67%) of 2-methyl-4-chloro-6-ethyl-7-(phenylmethyl)-7H-pyrrolo[2,3-d]pyrimidine as a solid. nmr (500 MHz, CDCl$_3$) δ1.29 (t, J=7.5 Hz, 3H), 2.61 (q, J=7.5 Hz, 2H), 2.74 (s, 3H), 5.45 (s, 2H), 6.33 (s, 1H), 7.03 (d, J=7.0 Hz, 2H), 7.28 (m, 3H)

P. Preparation of [[2-(methylthio)-6-ethyl-7-(phenylmethyl)-7H-pyrrolo[2,3-d]pyrimidin-4-yl]oxy]acetic Acid Methyl Ester

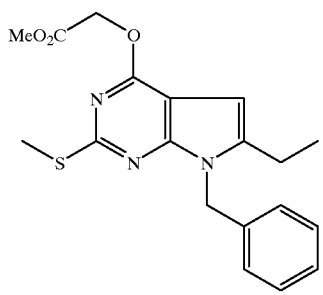

To a suspension of 0.70 g (28.3 mmol) of sodium hydride in 40 mL of benzene was added 1.90 g (24.5 mmol) of methyl glycolate and 6.00 g (18.9 mmol) of 2-(methylthio)-4-chloro-6-ethyl-7-(phenylmethyl)-7H-pyrrolo[2,3-d]pyrimidine. The mixture was heated at 60° C. and monitored by TLC (silica, methylene chloride) for conversion to product. After 3 days, an additional 0.70 g (28.3 mmol) of sodium hydride and 1.90 g (24.5 mmol) of methyl glycolate was added to the reaction. After an additional 3 days, the reaction was cooled to ambient temperature and partitioned by the addition of 100 mL of 2 M sodium hydrogen sulfate and 200 mL of ethyl acetate. The aqueous phase was extracted twice with 50 mL portions of ethyl acetate. The combined organic phases were dried with magnesium sulfate and concentrated to 7.85 g of yellow solid. The solid was purified by flash chromatography (500 g silica, step gradient from 1:1 heptane-methylene chloride to methylene chloride) to provide 6.35 g (90%) of [[2-(methylthio)-6-ethyl-7-(phenylmethyl)-7H-pyrrolo[2,3-d]pyrimidin-4-yl]oxy]acetic acid methyl ester as a white solid. nmr (500 MHz, CDCl$_3$) δ1.25 (t, J=7.5 Hz, 3H), 2.54 (s, 3H), 2.58 (q, J=7.5 Hz, 2H), 3.79 (s, 3H), 5.05 (s, 2H), 5.40 (s, 2H), 6.30 (s, 1H), 7.07 (d, J=7.1 Hz, 2H), 7.24 (m, 3H)

Q. Preparation of [[6-ethyl-7-(phenylmethyl)-7H-pyrrolo[2,3-d]pyrimidin-4-yl]oxy]acetic Acid Methyl Ester

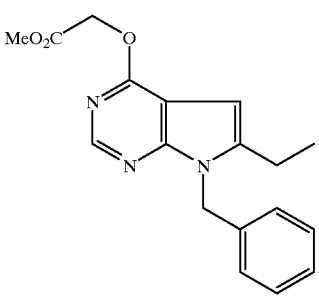

To a suspension of 165 mg (6.84 mmol) of sodium hydride in 12 mL of benzene was added 530 mg (5.93 mmol) of methyl glycolate and 1.24 g (4.56 mmol) of 4-chloro-6-ethyl-7-(phenylmethyl)-7H-pyrrolo[2,3-d]pyrimidine. The mixture was heated at 60° C. and monitored by TLC (silica, 7:3 heptane-ethyl acetate) for conversion to product. After 5 days the reaction was cooled to ambient temperature and partitioned by the addition of 10 mL of 2 M sodium hydrogen sulfate and 30 mL of ethyl acetate. The aqueous phase was extracted with 10 mL of ethyl acetate. The combined organic phases were dried with sodium sulfate and concentrated to 1.5 g of white solid. The solid was purified by flash chromatography (75 g silica, 3:2 heptane-ethyl acetate) to provide 1.04 g (70%) of [[6-ethyl-7-(phenylmethyl)-7H-pyrrolo[2,3-d]pyrimidin-4-yl]oxy]acetic acid methyl ester as a white solid. nmr (500 MHz, CDCl$_3$) δ1.28 (t, J=7.4 Hz, 3H), 2.63 (q, J=7.4 Hz, 2H), 3.81 (s, 3H), 5.10 (s, 2H), 5.47 (s, 2H), 6.41 (s, 1H), 7.03 (d, J=7.0 Hz, 2H), 7.27 (m, 3H), 8.39 (s, 1H)

R. Preparation of [[2-methyl-6-ethyl-7-(phenylmethyl)-7H-pyrrolo[2,3-d]pyrimidin-4-yl]oxy]acetic Acid Methyl Ester

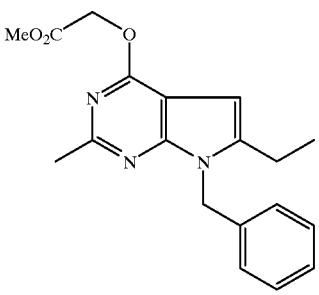

To a suspension of 240 mg (10.0 mmol) of sodium hydride in 15 mL of benzene was added 783 mg (8.69 mmol) of methyl glycolate and 1.91 g (6.68 mmol) of 2-methyl-4- chloro-6-ethyl-7-(phenylmethyl)-7H-pyrrolo[2,3-d]pyrimidine. The mixture was heated at 60° C. and monitored by TLC (silica, 7:3 heptane-ethyl acetate) for conversion to product. After 5 days the reaction was cooled to ambient temperature and partitioned by the addition of 10 mL of 2 M sodium hydrogen sulfate and 30 mL of ethyl acetate. The aqueous phase was extracted with 10 mL of ethyl acetate. The combined organic phases were dried with sodium sulfate and concentrated to 2.5 g of oil. The residue was purified by flash chromatography (200 g silica, 7:3 heptane-ethyl acetate) to provide 1.42 g (62%) of [[2-methyl-6-ethyl-7-(phenylmethyl)-7H-pyrrolo[2,3-d]pyrimidin-4-yl]oxy] acetic acid methyl ester as a white solid. nmr (500 MHz, CDCl$_3$) δ1.27 (t, J=7.4 Hz, 3H), 2.57 (q, J=7.4 Hz, 2H), 2.60 (s, 3H), 3.80 (s, 3H), 5.08 (s, 2H), 5.44 (s, 2H), 6.34 (s, 1H), 7.02 (d, J=7.1 Hz, 2H), 7.25 (m, 3H)

S. Preparation of [[2-(methylthio)-5-(aminooxoacetyl)-6-ethyl-7-(phenylmethyl)-7H-pyrrolo[2,3-d]pyrimidin-4-yl]oxy]acetic Acid Methyl Ester

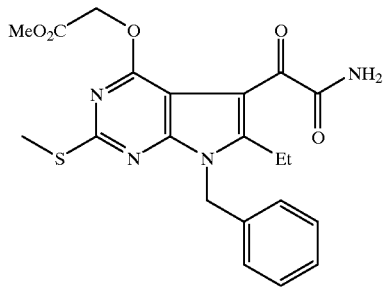

To a solution of 5.17 g (13.9 mmol) of [[2-(methylthio)-6-ethyl-7-(phenylmethyl)-7H-pyrrolo[2,3-d]pyrimidin-4-yl]oxy]acetic acid methyl ester in 100 mL of chloroform was added 3.64 mL of oxalyl chloride followed by 1.66 mL of pyridine. The reaction was stirred for 3 days at ambient temperature then poured into a solution prepared from 11 mL of concentrated ammonium hydroxide and 40 mL of water. The reaction was partitioned by the addition of 45 mL of water and 150 mL of methylene chloride. The organic phase was washed with 40 mL of water, dried with sodium sulfate, and concentrated to 5.90 g of yellow solid. The solid was first purified by flash chromatography (500 g of silica, ethyl acetate) and the product obtained was then slurried in 100 mL of methyl tert-butyl ether to provide 3.70 g (60%) of [[2-(methylthio)-5-(aminooxoacetyl)-6-ethyl-7-(phenylmethyl)-7H-pyrrolo[2,3-d]pyrimidin-4-yl]oxy] acetic acid methyl ester as a yellow solid. nmr (500 MHz, CDCl$_3$) δ1.12 (t, J=7.5 Hz, 3H), 2.52 (s, 3H), 2.91 (q, J=7.5 Hz, 2H), 3.78 (s, 3H), 5.02 (s, 2H), 5.46 (s, 2H), 5.66 (s, 1H), 6.56 (s, 1H), 7.16.(d, J=6.9 Hz, 2H), 7.28 (m, 3H)

T. Preparation of [[5-(aminooxoacetyl)-6-ethyl-7-(phenylmethyl)-7H-pyrrolo[2,3-d]pyrimidin-4-yl]oxy] acetic Acid Methyl Ester

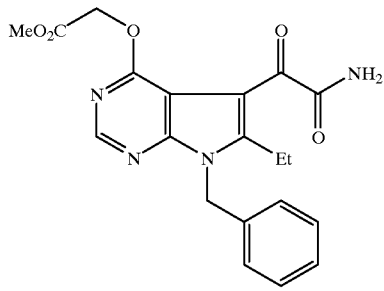

To a solution of 831 mg (2.55 mmol) of [[6-ethyl-7-(phenylmethyl)-7H-pyrrolo[2,3-d]pyrimidin-4-yl]oxy] acetic acid methyl ester in 20 mL of chloroform was added 0.67 mL of oxalyl chloride followed by 0.30 mL of pyridine. The reaction was stirred for 18 hours at ambient temperature then poured into a solution prepared from 2.0 mL of concentrated ammonium hydroxide and 8.0 mL of water. The reaction was partitioned by the addition of 20 mL of methylene chloride and 10 mL of water. The organic phase was dried with sodium sulfate and concentrated. The residue was purified by flash chromatography (100 g of silica, ethyl acetate) to provide 420 mg (51%) of [[6-ethyl-7-(phenylmethyl)-7H-pyrrolo[2, 3-d]pyrimidin-4-yl]oxy] acetic acid methyl ester and 455 mg (45%) of [[5-(aminooxoacetyl)-6-ethyl-7-(phenylmethyl)-7H-pyrrolo[2, 3-d]pyrimidin-4-yl]oxy]acetic acid methyl ester as a white solid. nmr (500 MHz, CDCl$_3$) δ1.13 (t, J=7.5 Hz, 3H), 2.95 (q, J=7.5 Hz, 2H), 3.77 (s, 3H), 5.06 (s, 2H), 5.53 (s, 2H), 6.28 (s, 1H), 6.70 (s, 1H), 7.13 (d, J=6.7 Hz, 2H), 7.27 (m, 3H), 8.46 (s, 1H)

U. Preparation of [[2-methyl-5-(aminooxoacetyl)-6-ethyl-7-(phenylmethyl)-7H-pyrrolo[2,3-d]pyrimidin-4-yl]oxy] acetic Acid Methyl Ester

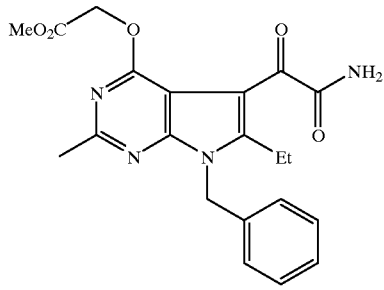

To a solution of 715 mg (2.10 mmol) of [[2-methyl-6-ethyl-7-(phenylmethyl)-7H-pyrrolo[2,3-d]pyrimidin-4-yl]oxy]acetic acid methyl ester in 15 mL of chloroform was added 0.55 mL of oxalyl chloride followed by 0.25 mL of pyridine. The reaction was stirred for 18 hours at ambient temperature then poured into a solution prepared from 1.7 mL of concentrated ammonium hydroxide and 5.8 mL of water. The reaction was partitioned by the addition of 15 mL of methylene chloride and a small amount of solid residue was removed by filtration. The organic phase was dried with sodium sulfate and concentrated to an off-white solid. The solid was purified by flash chromatography (100 g of silica, ethyl acetate) to provide 740 mg (86%) of [[2-methyl-5-(aminooxoacetyl)-6-ethyl-7-(phenylmethyl)-7H-pyrrolo[2, 3-d]pyrimidin-4-yl]oxy]acetic acid methyl ester as a white solid. nmr (500 MHz, CDCl$_3$) δ1.10 (t, J=7.5 Hz, 3H), 2.59 (s, 3H), 2.91 (q, J=7.5 Hz, 2H), 3.76 (s, 3H), 5.04 (s, 2H), 5.50 (s, 2H), 6.25 (s, 1H), 6.66 (s, 1H), 7.13 (d, J=6.9 Hz, 2H), 7.28 (m, 3H)

V. Preparation of [[2-(methylthio)-5-(aminooxoacetyl)-6-ethyl-7-(phenylmethyl)-7H-pyrrolo[2,3-d]pyrimidin-4-yl]oxy]Acetic Acid

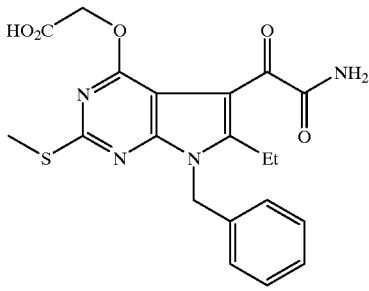

A suspension of 99.5 mg (0.225 mmol) of [[2-(methylthio)-5-(aminooxoacetyl)-6-ethyl-7-(phenylmethyl)-7H-pyrrolo[2,3-d]pyrimidin-4-yl]oxy]acetic acid methyl ester in 8.0 mL of ethanol was treated with 0.175 mL of 2 M sodium hydroxide and the mixture heated to 65° C. for 1 hour. The reaction mixture was cooled to ambient temperature and concentrated under vacuum to a white solid. The solid was dissolved in 12 mL of water and the product precipitated upon the addition of 0.40 mL of 1 M HCl. The solids were collected by filtration, washed with 10 mL of water, then dried in vacuo (40° C., 10 torr) to provide 78 mg (81%) of [[2-(methylthio)-5-(aminooxoacetyl)-6-ethyl-7-(phenylmethyl)-7H-pyrrolo[2,3-d]pyrimidin-4-yl]oxy]acetic acid as a white solid. nmr (500 MHz, dmso-d$_6$) δ1.00 (t, J=7.4 Hz, 3H), 2.49 (s, 3H), 2.91 (q, J=7.4 Hz, 2H), 4.89 (s, 2H), 5.52 (s, 2H), 7.15 (d, J=7.2 Hz, 2H), 7.32 (m, 3H), 7.55 (s, 1H), 7.97 (s, 1H), 13.02 (bs, 1H)

W. Preparation of [[5-(aminooxoacetyl)-6-ethyl-7-(phenylmethyl)-7H-pyrrolo[2,3-d]pyrimidin-4-yl]oxy] acetic Acid

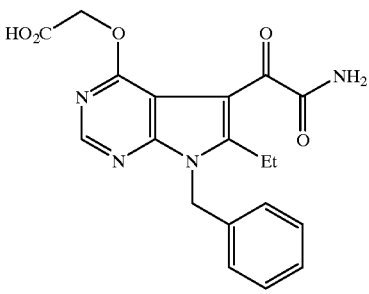

A mixture of 215 mg (0.542 mmol) of [[5-(aminooxoacetyl)-6-ethyl-7-(phenylmethyl)-7H-pyrrolo[2,3-d]pyrimidin-4-yl]oxy]acetic acid methyl ester and 3 mL of methanol were treated with 0.406 mL of 2 M sodium hydroxide and heated to 55° C. for 3 hours. The reaction was cooled to ambient temperature, 1.0 mL of 1 M HCl was added and the resulting slurry was concentrated under vacuum. The crude solid was combined with 20 mL of water and stirred for 20 minutes. The precipitate was collected by filtration, washed with 20 mL of water, and dried in vacuo (40° C., 10 torr) to provide 190 mg (91.7%) of [[5-(aminooxoacetyl)-6-ethyl-7-(phenylmethyl)-7H-pyrrolo[2,3-d]pyrimidin-4-yl]oxy]acetic acid. as a white solid. nmr (500 MHz, dmso-d$_6$) δ1.01 (t, J=7.4 Hz, 3H), 2.95 (q, J=7.4 Hz, 2H), 4.93 (s, 2H), 5.60 (s, 2H), 7.13 (d, J=7.2 Hz, 2H), 7.31 (m, 3H), 7.56 (s, 1H), 7.98 (s, 1H), 8.46 (s, 1H) 12.99 (bs, 1H)

X. Preparation of [[2-methyl-5-(aminooxoacetyl)-6-ethyl-7-(phenylmethyl)-7H-pyrrolo[2,3-d]pyrimidin-4-yl]oxy] acetic Acid

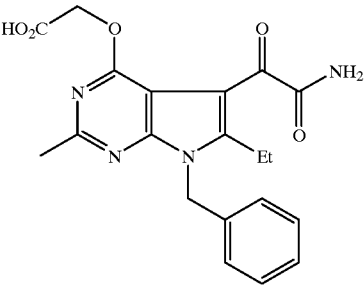

A mixture of 225 mg (0.548 mmol) of [[2-methyl-5-(aminooxoacetyl)-6-ethyl-7-(phenylmethyl)-7H-pyrrolo[2,3-d]pyrimidin-4-yl]oxy]acetic acid methyl ester and 3 mL of methanol was treated with 0.411 mL of 2 M sodium hydroxide and heated to 55° C. for 3 hours. The reaction was cooled to ambient temperature, 1.0 mL of 1 M HCl was added and the resulting slurry was concentrated under vacuum. The crude solid was combined with 20 mL of water and stirred for 20 minutes. The precipitate was collected by filtration, washed with 20 mL of water, and dried in vacuo (40° C., 10 torr) to provide 190 mg (97.5%) of [[2-methyl-5-5(aminooxoacetyl)-6-ethyl-7-(phenylmethyl)-7H-pyrrolo[2,3-d]pyrimidin-4-yl]oxy]acetic acid as a white solid. nmr (500 MHz, dmso-d$_6$) δ0.98 (t, J=7.4 Hz, 3H), 2.51 (s, 3H), 2.90 (q, J=7.4 Hz, 2H), 4.90 (s, 2H), 5.56 (s, 2H), 7.11 (d, J=6.9 Hz, 2H), 7.31 (m, 3H), 7.52 (s, 1H), 7.94 (s, 1H), 12.92 (bs, 1H)

Y. Preparation of [[2-(methylsulfonyl)-5-(aminooxoacetyl)-6-ethyl-7-(phenylmethyl)-7H-pyrrolo[2,3-d]pyrimidin-4-yl]oxy]acetic Acid Methyl Ester

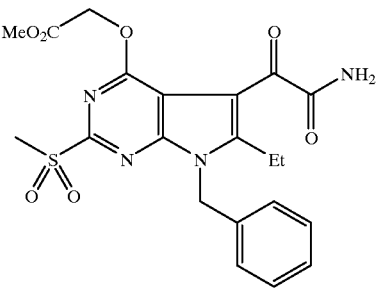

A solution of 44 mg (0.10 mmol) of [[2-(methylthio)-5-(aminooxoacetyl)-6-ethyl-7-(phenylmethyl)-7H-pyrrolo[2,3-d]pyrimidin-4-yl]oxy]acetic acid methyl ester in 1.0 mL of glacial acetic acid was combined with 0.018 mL of 30% hydrogen peroxide. The solution was heated to 60° C. for 18 hours, cooled to ambient temperature then concentrated under vacuum to a thick oil. The oil was purified by flash chromatography (2.2 g silica, ethyl acetate) to provide 32 mg (68%) of [[2-(methylsulfonyl)-5-(aminooxoacetyl)-6-ethyl-7-(phenylmethyl)-7H-pyrrolo[2,3-d]pyrimidin-4-yl]oxy]acetic acid methyl ester as a white solid. nmr (500 MHz, CDCl$_3$) δ1.14 (t, J=7.5 Hz, 3H), 2.97 (q, J=7.5 Hz, 2H), 3.27

(s, 3H), 3.78 (s, 3H), 5.11 (s, 2H), 5.58 (s, 2H), 5.93 (s, 1H), 6.70 (s, 1H), 7.15 (d, J=7.2 Hz, 2H), 7.31 (m, 3H)

Z. Preparation of [[2-(phenylthio)-5-(aminooxoacetyl)-6-ethyl-7-(phenylmethyl)-7H-pyrrolo[2,3-d]pyrimidin-4-yl]oxy]acetic Acid Methyl Ester

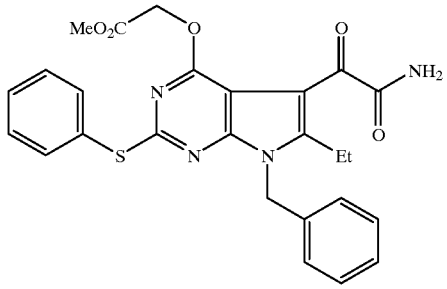

To a slurry of 5.4 mg (0.23 mmol) of sodium hydride in 1.0 mL of tetrahydrofuran was added 0.025 mL of thiophenol followed by 100 mg (0.21 mmol) of [[2-(methylsulfonyl)-5-(aminooxoacetyl)-6-ethyl-7-(phenylmethyl)-7H-pyrrolo[2,3-d]pyrimidin-4-yl]oxy]acetic acid methyl ester and the mixture heated to 55° C. for 18 hours. The reaction was cooled to ambient temperature and partitioned between 10 mL of methylene chloride and 10 mL of 0.2 M sodium hydrogen sulfate. The organic portion was dried with magnesium sulfate and concentrated to a solid. The crude material was purified by flash chromatography (5.0 g silica, ethyl acetate) to provide 52 mg (49%) of [[2-(phenylthio)-5-(aminooxoacetyl)-6-ethyl-7-(phenylmethyl)-7H-pyrrolo[2,3-d]pyrimidin-4-yl]oxy]acetic acid methyl ester as a white solid. nmr (500 MHz, CDCl$_3$) δ1.14 (t, J=7.4 Hz, 3H), 2.94 (q, J=7.4 Hz, 2H), 3.72 (s, 3H), 4.81 (s, 2H), 5.34 (s, 2H), 5.59 (s, 1H), 6.54 (s, 1H), 7.10 (m, 2H), 7.28 (m, 3H), 7.40 (m, 3H), 7.62 (m, 2H)

AA. Preparation of [12-(phenylthio)-5-(aminooxoacetyl)-6-ethyl-7-(phenylmethyl)-7H-pyrrolo[2,3-d]pyrimidin-4-yl]oxylacetic Acid

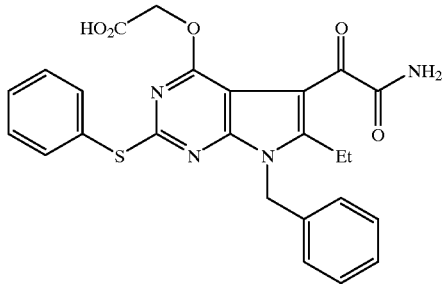

A mixture of 52 mg (0.10 mmol) of [[2-(phenylthio)-5-(aminooxoacetyl)-6-ethyl-7-(phenylmethyl)-7H-pyrrolo[2,3-d]pyrimidin-4-yl]oxy]acetic acid methyl ester, 0.5 mL of 2 M sodium hydroxide, and 2.0 mL of methanol was stirred at ambient temperature for 18 hours. The reaction was diluted with 10 mL of water the product precipitated upon neutralization to pH 3.5 with 1 M HCl. The precipitate was collected by filtration, washed with 10 mL of water, and dried to 41 mg (83%) of [[2-(phenylthio)-5-(aminooxoacetyl)-6-ethyl-7-(phenylmethyl)-7H-pyrrolo[2,3-d]pyrimidin-4-yl]oxy]acetic acid as a white solid. nmr (500 MHz, dmso-d$_6$) δ1.01 (t, J=7.3 Hz, 3H), 2.91 (q, J=7.3 Hz, 2H), 4.43 (s, 2H), 5.30 (s, 2H), 7.06 (d, J=7.2 Hz, 2H), 7.30 (m, 3H), 7.41 (m, 3H), 7.62 (m, 3H), 7.93 (s, 1H)

AB. Preparation of [[2-methoxy-5-(aminooxoacetyl)-6-ethyl-7-(phenylmethyl)-7H-pyrrolo[2,3-d]pyrimidin-4-yl]oxy]acetic Acid Methyl Ester

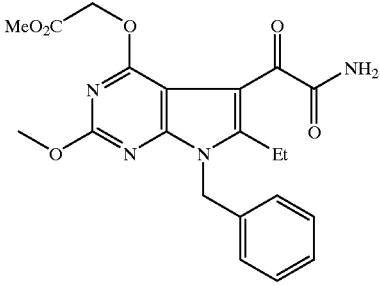

To a solution of 150 mg (0.316 mmol) of [[2-(methylsulfonyl)-5-(aminooxoacetyl)-6-ethyl-7-(phenylmethyl)-7H-pyrrolo[2,3-d]pyrimidin-4-yl]oxy] acetic acid methyl ester in 3 mL of tetrahydrofuran and 0.5 mL of methanol was added 4 drops of 28% sodium methoxide in methanol solution. The reaction was stirred at ambient temperature for 3 hours. The reaction was quenched by the addition of 3 mL of saturated sodium bicarbonate solution and the phases separated. The organic phase was dried with sodium sulfate and concentrated to a yellow solid. The solid was purified by flash chromatography (5.0 g silica, ethyl acetate) to provide 41 mg of [[2-methoxy-5-(aminooxoacetyl)-6-ethyl-7-(phenylmethyl)-7H-pyrrolo[2,3-d]pyrimidin-4-yl]oxy]acetic acid methyl ester as an off white solid. nmr (500 MHz, CDCl$_3$) δ1.11 (t, J=7.5 Hz, 3H), 2.90 (q, J=7.5 Hz, 2H), 3.77 (s, 3H), 3.96 (s, 3H), 5.04 (s, 2H), 5.43 (s, 2H), 5.74 (s, 1H), 6.58 (s, 1H), 7.16 (d, J=7.0 Hz, 2H), 7.29 (m, 3H)

AC. Preparation of [[2-methoxy-5-(aminooxoacetyl)-6-ethyl-7-(phenylmethyl)-7H-pyrrolo[2,3-d]pyrimidin-4-yl]oxy]acetic Acid

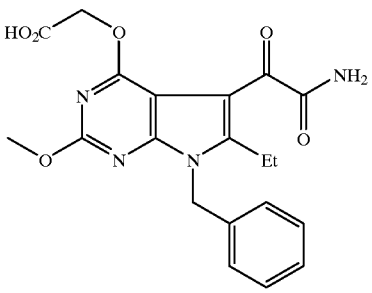

A suspension of 40 mg of [[2-methoxy-5-(aminooxoacetyl)-6-ethyl-7-(phenylmethyl)-7H-pyrrolo[2,3-d]pyrimidin-4-yl]oxy]acetic acid methyl ester, 2.0 mL of methanol and 0.5 mL of 2 M sodium hydroxide were stirred at ambient temperature for 18 hours. The reaction was diluted with 10 mL of water and then adjusted to pH 4 with 1 M HCl providing a precipitate. The precipitate was collected by filtration and washed with 5 mL of water and dried in vacuo (40° C., 10 torr) to provide 22 mg of [[2-methoxy-5-(aminooxoacetyl)-6-ethyl-7-(phenylmethyl)-7H-pyrrolo[2,3-d]pyrimidin-4-yl]oxy]acetic acid as a white solid. nmr (500 MHz, dmso-d$_6$) δ0.98 (t, J=7.5 Hz, 3H), 2.89 (q, J=7.5 Hz, 2H), 3.87 (s, 3H), 4.87 (s, 2H), 5.48 (s, 2H), 7.17 (d, J=7.3 Hz, 2H), 7.31 (m, 3H), 7.50 (s, 1H), 7.93 (s, 1H), 12.89 (bs, 1H)

AD. Preparation of 2-(methylthio)-4-chloro-6-ethyl-7-([1,1'-biphenyl]-2-ylmethyl)-7H-pyrrolo[2,3-d]pyrimidine

37

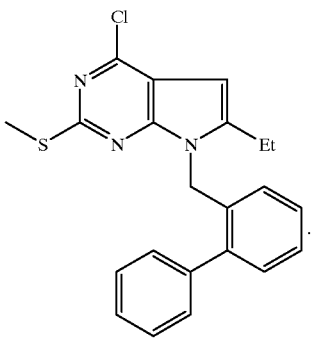

A solution of 500 mg (2.19 mmol) of 4-chloro-6-ethyl-1H-pyrrolo[2,3-d]pyrimidine in 13 mL of tetrahydrofuran (THF) was added to a 0° C. slurry of 1.11 g (4.39 mmol) of 2-phenylbenzyl bromide and 105 mg (4.39 mmol) of sodium hydride in 7 mL of THF. The reaction was allowed to warm to ambient temperature and stirred for 18 hours. The reaction was quenched by the addition of 15 mL of brine. The organic phase was dried with magnesium sulfate and concentrated to an oil. The product precipitated upon addition of hexanes to provide 253 mg (29%) of 2-(methylthio)-4-chloro-6-ethyl-7-([1,1'-biphenyl]-2-ylmethyl)-7H-pyrrolo[2,3-d]pyrimidine as a light tan solid. nmr (300 MHz, CDCl$_3$) δ1.13 (t, J=7.4 Hz, 3H), 2.30 (q, J=7.4 Hz, 2H), 2.58 (s, 3H), 5.35 (s, 2H), 6.02 (s, 1H), 6.65 (d, J=7.0 Hz, 1H), 7.2–7.6 (m, 8H)

AE. Preparation of [[6-ethyl-7-([1,1'-biphenyl]-2-ylmethyl)-7H-pyrrolo[2,3-dpyrimidin-4-yl]oxy]acetic Acid Methyl Ester

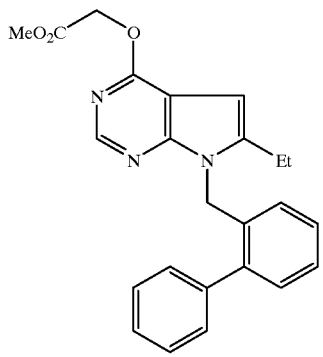

To a suspension of 85 mg (3.55 mmol) of sodium hydride in 4 mL of benzene was added 326 mg (3.55 mmol) of methyl glycolate and a solution of 200 mg (0.507 mmol) of 2-(methylthio)-4-chloro-6-ethyl-7-([1,1'-biphenyl]-2-ylmethyl)-7H-pyrrolo[2,3-d]pyrimidine in 8 ml of benzene. The mixture was heated at 60° C. and monitored by TLC (silica, methylene chloride) for conversion to product. After 70 hours, the reaction was cooled to ambient temperature and partitioned by the addition of 15 mL of 2 M sodium hydrogen sulfate and 15 mL of ethyl acetate. The aqueous phase was extracted twice with 7 mL portions of ethyl acetate. The combined organic phases were dried with sodium sulfate and concentrated to provide 380 mg of yellow oil containing [[2-(methylthio)-6-ethyl-7-([1,1'-biphenyl]-2-ylmethyl)-7H-pyrrolo[2,3-d]pyrimidin-4-yl]oxy]acetic acid methyl ester as the major component. The crude oil was dissolved in 30 mL of ethanol, treated with 2.28 g of Raney Ni, then the mixture heated to reflux. After 18 hours, the solids were removed by filtration through a

38 filter aid and the reaction concentrated to an oil. The oil was purified by flash chromatography (46 g silica, hexanes-ethyl acetate gradient 100:0 to 2:1) to provide 203 mg (quantitative yield for 2 steps) of [[6-ethyl-7-([1,1'-biphenyl]-2-ylmethyl)-7H-pyrrolo[2,3-d]pyrimidin-4-yl]oxy]acetic acid methyl ester as an oil. nmr (300 MHz, CDCl$_3$) δ1.14 (t, J=7.5 Hz, 3H), 2.32 (q, J=7.5 Hz, 2H), 3.79 (s, 3H), 5.08 (s, 2H), 5.38 (s, 2H), 6.37 (s, 1H), 6.5 (d, J=7.1 Hz, 1H), 7.1–7.6 (m, 8H), 8.37 (s, 1H)

AF. Preparation of [[5-(aminooxoacetyl)-6-ethyl-7-([1,1'-biphenyl]-2-ylmethyl)-7H-pyrrolo[2,3-d]pyrimidin-4-yl]oxy]acetic Acid Methyl Ester

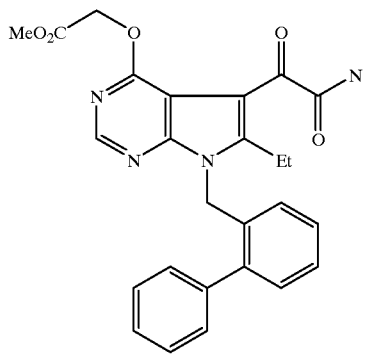

To a solution of 203 mg (0.505 mmol) of [[6-ethyl-7-(1,1'-biphenyl]-2-ylmethyl)-7H-pyrrolo[2,3-d]pyrimidin-4-yl]oxy]acetic acid methyl ester in 5 mL of chloroform was added 0.14 mL of oxalyl chloride followed by 0.06 mL of pyridine. The reaction was stirred for 24 hours at ambient temperature then an additional 0.14 mL of oxalyl chloride and 0.06 mL of pyridine were added. This mixture was stirred and additional 2 days then quenched into 4.0 mL of dilute ammonium hydroxide. The product was extracted into 5.0 mL of methylene chloride. The organic phase was dried with sodium sulfate and concentrated to 200 mg of yellow oil. The residue was purified by flash chromatography (20 g of silica, ethyl acetate) to provide 150 mg (63%) of [[5-(aminooxoacetyl)-6-ethyl-7-([1,1'-biphenyl]-2-ylmethyl)-7H-pyrrolo[2,3-d]pyrimidin-4-yl]oxy]acetic acid methyl ester as an oil. nmr (300 MHz, CDCl$_3$) δ1.13 (t, J=7.5 Hz, 3H), 2.63 (q, J=7.5 Hz, 2H), 3.76 (s, 3H), 5.05 (s, 2H), 5.48 (s, 2H), 6.28 (s, 1H), 6.68 (s, 1H), 6.78 (d, 1H), 7.1–7.6 (m, J=6.7, 8H), 8.45 (s, 1H)

AG. Preparation of [[5-(aminooxoacetyl)-6-ethyl-7-([1,1'-biphenyl]-2-ylmethyl)-7H-pyrrolo[2,3-d]pyrimidin-4-yl]oxy]acetic Acid

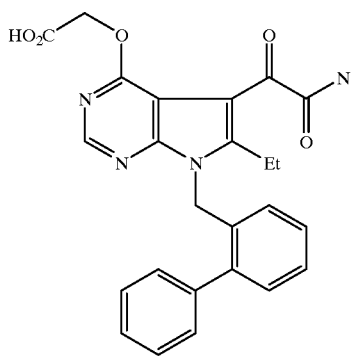

A mixture of 150 mg (0.317 mmol) of [[5-(aminooxoacetyl)-6-ethyl-7-([1,1'-biphenyl] -2-ylmethyl)-

7H-pyrrolo[2,3-d]pyrimidin-4-yl]oxy]acetic acid methyl ester and 10 mL of methanol were treated with 0.95 mL of 2 M sodium hydroxide and heated to reflux for 4 hours. The reaction was cooled to ambient temperature then adjusted to pH 2 by the addition of 1 M HCl. The mixture was concentrated to a minimum volume and the residual liquid decanted from the solids. The solids were dried in vacuo to provide 92 mg (63%) of [[5-(aminooxoacetyl)-6-ethyl-7-([1,1'-biphenyl]-2-ylmethyl)-7H-pyrrolo[2,3-d]pyrimidin-4-yl]oxy]acetic acid as a tan foam. nmr (300 MHz, dmso-$d_6$) δ1.15 (t, J=7.4 Hz, 3H), 2.64 (q, J=7.4 Hz, 2H), 4.90 (s, 2H), 5.46 (s, 2H), 6.60 (d, J=7.2 Hz, 1H), 7.2–7.6 (m, 9H), 7.99 (s, 1H), 8.43 (s, 1H)

AH. Preparation of 2-(methylthio)-4-chloro-6-ethyl-7-[(3-fluorophenyl)methyl]-7H-pyrrolo[2,3-d]pyrimidine

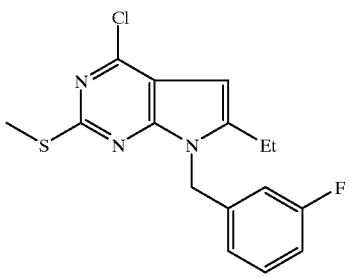

A solution of 300 mg (1.31 mmol) of 2-(methylthio)-4-chloro-6-ethyl-1H-pyrrolo[2,3-d]pyrimidine in 10 mL of tetrahydrofuran (THF) was added to a 0° C. slurry of 377 mg (1.97 mmol) of 3-fluorobenzyl bromide and 55 mg (2.30 mmol) of sodium hydride in 10 mL of THF. The reaction was allowed to warm to ambient temperature and stirred for 16 hours. The reaction was quenched by the addition of 15 mL of brine. The organic phase was dried with sodium sulfate and concentrated to an oil. The product precipitated upon addition of hexanes to provide 384 mg (87%) of 2-(methylthio)-4-chloro-6-ethyl-7-[(3-fluorophenyl)methyl]-7H-pyrrolo[2,3-d]pyrimidine as a light tan solid. nmr (300 MHz, CDCl$_3$) δ1.11 (t, 3H), 2.58 (s, 3H), 2.59 (q, 2H), 5.39 (s, 2H), 6.29 (s, 1H), 6.75 (d, 1H), 6.85 (d, 1H), 6.96 (dt, 1H), 7.26 (dt, 1H)

AI. Preparation of [[2-(methylthio)-6-ethyl-7-[(3-fluorophenyl)methyl]-7H-pyrrolo[2,3-d]pyrimidin-4-yl]oxy]acetic Acid Methyl Ester

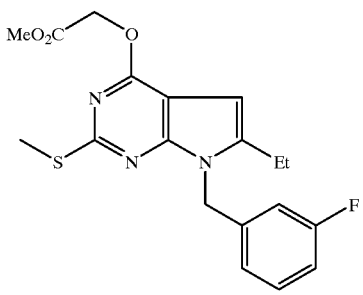

To a suspension of 82 mg (3.43 mmol) of sodium hydride in 4 mL of benzene was added 315 mg (3.43 mmol) of methyl glycolate and a solution of 384 mg (1.14 mmol) of 2-(methylthio)-4-chloro-6-ethyl-7-[(3-fluorophenyl)methyl]-7H-pyrrolo[2,3-d]pyrimidine in 4 ml of benzene. The mixture was heated at 57° C. and monitored by TLC (silica, methylene chloride) for conversion to product. After 2 days, the reaction was cooled to ambient temperature and partitioned by the addition of 15 mL of 2 M sodium hydrogen sulfate and 15 mL of ethyl acetate. The aqueous phase was extracted twice with 7 mL portions of ethyl acetate. The combined organic phases were dried with sodium sulfate and concentrated 600 mg of solid. The product was purified by flash chromatography (54 g silica, hexane-ethyl acetate gradient 100:0 to 75:25) to provide 211 mg (48%) of [[2-(methylthio)-6-ethyl-7-[(3-fluorophenyl)methyl]-7H-pyrrolo[2,3-d]pyrimidin-4-yl]oxy]acetic acid methyl ester as a white solid. nmr (300 MHz, CDCl$_3$) δ1.14 (t, 3H), 2.53 (s, 3H), 2.55 (q, 2H), 3.88 (s, 3H), 5.04 (s, 2H), 5.36 (s, 2H), 6.30 (s, 1H), 6.75 (d, 1H), 6.85 (d, 1H), 6.96 (dt, 1H), 7.26 (dt, 1H)

AJ. Preparation of [[6-ethyl-7-[(3-fluorophenyl)methyl]-7H-pyrrolo[2,3-d]pyrimidin-4-yl]oxy]acetic Acid Methyl Ester

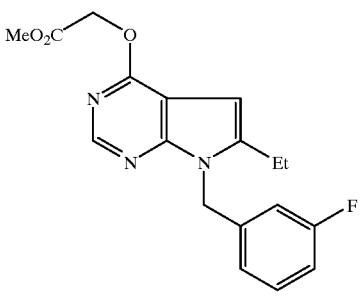

A suspension of 211 mg (0.541 mmol) of [[2-(methylthio)-6-ethyl-7-[(3-fluorophenyl)methyl]-7H-pyrrolo[2,3-d]pyrimidin-4-yl]oxy]acetic acid methyl ester in 20 mL of ethanol was treated with 1.27 g of Raney Ni and heated to reflux. After 24 hours, the solids were removed by filtration through a filter aid and the reaction concentrated to provide 140 mg (75%) of [[6-ethyl-7-[(3-fluorophenyl)methyl]-7H-pyrrolo[2,3-d]pyrimidin-4-yl]oxy]acetic acid methyl ester as a solid. nmr (300 MHz, CDCl$_3$) δ1.20 (t, 3H), 2.62 (q, 2H), 3.79 (s, 3H), 5.09 (s, 2H), 5.45 (s, 2H), 6.42 (s, 1H), 6.72 (d, 1H), 6.82 (d, 1H), 6.93 (dt, 1H), 7.26 (dt, 1H), 8.37 (s, 1H)

AK. Preparation of [[5-(aminooxoacetyl)-6-ethyl-7-[(3-fluorophenyl)methyl]-7H-pyrrolo[2,3-d]pyrimidin-4-yl]oxy]acetic Acid Methyl Ester

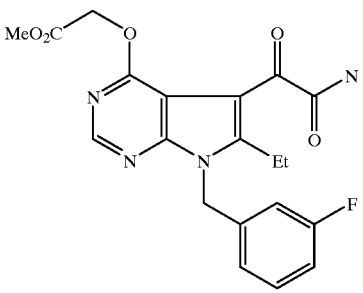

To a suspension of 140 mg (0.407 mmol) of [[6-ethyl-7-[(3-fluorophenyl)methyl]-7H-pyrrolo[2,3-d]pyrimidin-4-yl]oxy]acetic acid methyl ester in 5 mL of chloroform was added 0.053 mL of oxalyl chloride followed by 0.10 mL of pyridine. The reaction was stirred for 30 hours at ambient temperature then an additional 0.10 mL of oxalyl chloride was added. This mixture was stirred and additional 2 days then quenched into 4.0 mL of dilute ammonium hydroxide. The product was extracted into 4.0 mL of methylene chloride. The organic phase was washed with saturated sodium chloride, dried with sodium sulfate and concentrated to 300 mg of crude oil. The residue was purified by flash chromatography (30 g of silica, hexanes-ethyl acetate gradient 100:0 to 25:75) to provide 28 mg (17%) of [[5-(aminooxoacetyl)-6-ethyl-7-[(3-fluorophenyl)methyl]-7H-pyrrolo[2,3-d]pyrimidin-4-yl]oxy]acetic acid methyl ester as a solid. nmr (300 MHz, CDCl$_3$) δ1.20 (t, 3H), 2.88 (q, 2H), 3.70 (s, 3H), 4.98 (s, 2H), 5.44 (s, 2H), 6.00 (s, 1H), 6.60 (s, 1H), 6.84 (m, 2H), 6.90 (dt, 1H), 7.20 (dt, 1H), 8.39 (s, 1H)

AL. Preparation of [[5-(aminooxoacetyl)-6-ethyl-7-[(3-fluorophenyl)methyl]-7H-pyrrolo[2,3-d]pyrimidin-4-yl]oxy]acetic Acid

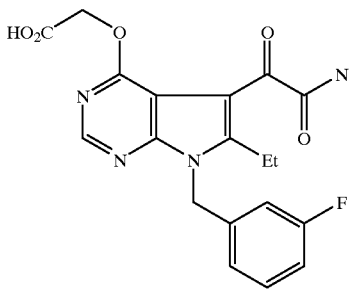

A mixture of 28 mg (0.067 mmol) of [[5-(aminooxoacetyl)-6-ethyl-7-[(3-fluorophenyl)methyl]-7H-pyrrolo[2,3-d]pyrimidin-4-yl]oxy]acetic acid methyl ester and 5 mL of methanol were treated with 0.05 mL of 2 M sodium hydroxide and stirred at ambient temperature for 22 hours. The reaction was adjusted to pH 3 by the addition of 1 M HCl and concentrated to provide 10 mg (40%) of [[5-(aminooxoacetyl)-6-ethyl-7-[(3-fluorophenyl)methyl]-7H-pyrrolo[2,3-d]pyrimidin-4-yl]oxy]acetic acid as a white solid. nmr (300 MHz, dmso-d$_6$) δ1.02 (t, 3H), 2.94 (q, 2H), 4.91 (s, 2H), 5.59 (s, 2H), 6.90 (d, 1H), 7.04 (d, 1H), 7.10 (dt, 1H), 7.36 (dt, 1H), 7.60 (br s, 1H), 8.02 (br s, 1H), 8.45 (s, 1H)

AM. Preparation of [[2-(methylthio)-6-ethyl-7-([1,1'-biphenyl]-2-ylmethyl)-7H-pyrrolo[2,3-d]pyrimidin-4-yl]oxy]acetic Acid Methyl Ester

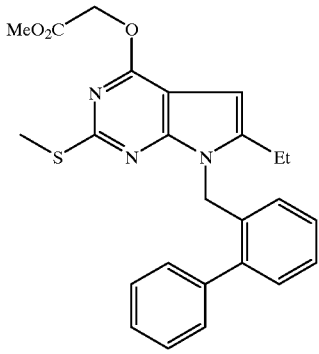

To a suspension of 64 mg (2.66 mmol) of sodium hydride in 5 mL of benzene was added 200 mg (2.22 mmol) of methyl glycolate and a solution of 350 mg (0.89 mmol) of 2-(methylthio)-4-chloro-6-ethyl-7-([1,1'-biphenyl]-2-ylmethyl)-7H-pyrrolo[2,3-d]pyrimidine in 2.5 ml of benzene then the mixture heated to 60° C. The reaction was monitored for conversion to product by TLC (silica, methylene chloride). Additional sodium hydride (96 mg) and methyl glycolate (360 mg) were added in portions over 4 days. The reaction was cooled to ambient temperature and partitioned by the addition of 15 mL of 2 M sodium hydrogen sulfate and 15 mL of ethyl acetate. The aqueous phase was extracted twice with 7 mL portions of ethyl acetate. The combined organic phases were dried with sodium sulfate and concentrated. The product was purified by flash chromatography (53 g silica, hexanes-ethyl acetate gradient 100:0 to 85:15) to provide 187 mg (47%) of [[2-(methylthio)-6-ethyl-7-([1,1'-biphenyl]-2-ylmethyl)-7H-pyrrolo[2,3-d]pyrimidin-4-yl]oxy]acetic acid methyl ester as a solid. nmr (300 MHz, CDCl$_3$) δ1.10 (t, 3H), 2.16 (q, 2H), 2.52 (s, 3H), 3.80 (s, 3H), 5.03 (s, 2H), 5.32 (s, 2H), 6.25 (s, 1H), 6.62 (d, 1H), 7.1–7.6 (m, 8H)

AN. Preparation of [[2-(methylthio)-5-(aminooxoacetyl)-6-ethyl-7-([1,1'-biphenyl]-2-ylmethyl)-7H-pyrrolo[2,3-d]pyrimidin-4-yl]oxy]acetic Acid Methyl Ester

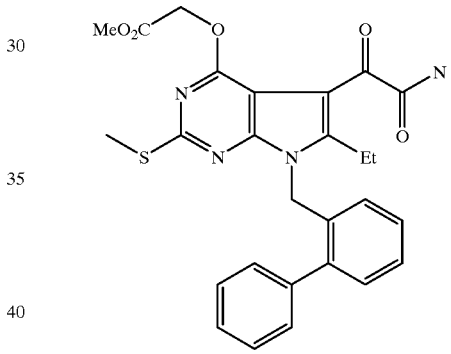

To a solution of 187 mg (0.417 mmol) of [[2-(methylthio)-6-ethyl-7-([1,1'-biphenyl]-2-ylmethyl)-7H-pyrrolo[2,3-d]pyrimidin-4-yl]oxy]acetic acid methyl ester in 5 mL of chloroform was added 0.11 mL of oxalyl chloride followed by 0.05 mL of pyridine. The mixture was stirred for 2 days then quenched into 4.0 mL of dilute ammonium hydroxide. The product was extracted into 5.0 mL of methylene chloride. The organic phase was dried with sodium sulfate and concentrated to 500 mg of yellow oil. The residue was purified by flash chromatography (5 g of silica, ethyl acetate) to provide 240 mg of [[2-(methylthio)-5-(aminooxoacetyl)-6-ethyl-7-([1,1'-biphenyl]-2-ylmethyl)-7H-pyrrolo[2,3-d]pyrimidin-4-yl]oxy]acetic acid methyl ester as an oil. nmr (300 MHz, CDCl$_3$) δ0.82 (t, 3H), 2.52 (s, 3H), 2.59 (q, 2H), 3.77 (s, 3H), 5.00 (s, 2H), 5.40 (s, 2H), 5.68 (s, 1H), 6.54 (s, 1H), 6.85 (d, 1H), 7.1–7.6 (m, J=6.7, 8H)

AO. Preparation of [[2-(methylthio)-5-(aminooxoacetyl)-6-ethyl-7-([1,1'-biphenyl]-2-ylmethyl)-7H-pyrrolo[2,3-d]pyrimidin-4-yl]oxy]acetic Acid

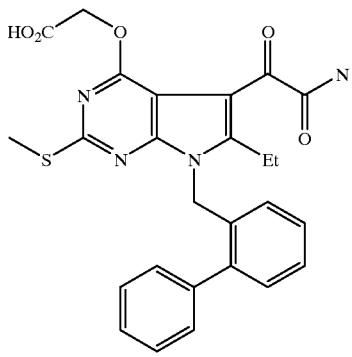

A mixture of 240 mg (0.462 mmol) of [[2-(methylthio)-5-(aminooxoacetyl)-6-ethyl-7-([1,1'-biphenyl]-2-ylmethyl)-7H-pyrrolo[2,3-d]pyrimidin-4-yl]oxy]acetic acid methyl ester and 15 mL of methanol was treated with 0.35 mL of 2 M sodium hydroxide and stirred at ambient temperature for 24 hours. The reaction was then adjusted to pH 2 by the addition of 1 M HCl. The mixture was concentrated and the solids were dried in vacuo to provide 162 mg (69%) of [[2-(methylthio)-5-(aminooxoacetyl)-6-ethyl-7-([1,1'-biphenyl] -2-ylmethyl)-7H-pyrrolo[2,3-d]pyrimidin-4-yl]oxy]acetic acid as a solid. nmr (300 MHz, dmso-$d_6$) δ0.78 (t, 3H), 2.44 (s, 3H), 2.60 (q, 2H), 4.84 (s, 2H), 5.40 (s, 2H), 6.74 (d, 1H), 7.2–7.5 (m, 9H), 7.60 (s, 1H), 7.97 (s, 1H)

AP. Preparation of [[2-(methylthio)-5-(aminooxoacetyl)-6-ethyl-7-[(3-fluorophenyl)methyl]-7H-pyrrolo[2,3-d]pyrimidin-4-yl]oxy]acetic Acid Methyl Ester

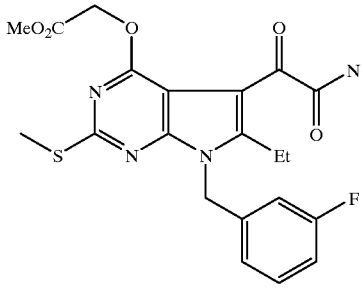

To a solution of 300 mg (0.770 mmol) of [[2-(methylthio)-6-ethyl-7-[(3-fluorophenyl)methyl]-7H-pyrrolo[2,3-d]pyrimidin-4-yl]oxy]acetic acid methyl ester in 5 mL of chloroform was added 0.21 mL of oxalyl chloride followed by 0.09 mL of pyridine. The reaction was stirred for 2 days at ambient temperature then quenched into 4.0 mL of dilute ammonium hydroxide. The product was extracted into 4.0 mL of methylene chloride. The organic phase was washed with water, dried with sodium sulfate and concentrated to 430 mg of tan solid. The residue was purified by flash chromatography (45 g of silica, ethyl acetate) to provide 260 mg (73%) of [[2-(methylthio)-5-(aminooxoacetyl)-6-ethyl-7-[(3-fluorophenyl)methyl]-7H-pyrrolo[2,3-d]pyrimidin-4-yl]oxy]acetic acid methyl ester as a solid. nmr (300 MHz, dmso-$d_6$) δ1.00 (t, 3H), 2.45 (s, 3H), 2.90 (q, 2H), 3.65 (s, 3H), 4.97 (s, 2H), 5.52 (s, 2H), 6.91 (d, 1H), 7.03 (d, 1H), 7.12 (dt, 1H), 7.47 (dt, 1H), 7.60 (s, 1H), 8.01 (s, 1H)

AQ. Preparation of [[2-(methylthio)-5-(aminooxoacetyl)-6-ethyl-7-[(3-fluorophenyl)methyl]-7H-pyrrolo[2,3-d]pyrimidin-4-yl]oxy]acetic Acid

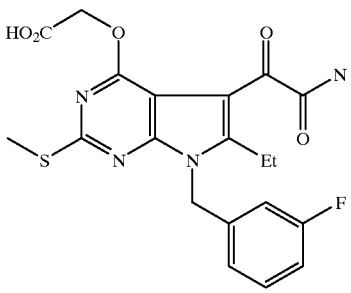

A mixture of 260 mg (0.564 mmol) of [[2-(methylthio)-5-(aminooxoacetyl)-6-ethyl-7-[(3-fluorophenyl)methyl]-7H-pyrrolo[2,3-d]pyrimidin-4-yl]oxy]acetic acid methyl ester and 25 mL of methanol were treated with 0.42 mL of 2 M sodium hydroxide and stirred at reflux for 3 hours. The reaction was cooled to ambient temperature. The product precipitated upon addition of 1 M HCl and was collected by filtration. The solids were washed with water and dried in vacuo to provide 176 mg (73%) of [[2-(methylthio)-5-(aminooxoacetyl)-6-ethyl-7-[(3-fluorophenyl)methyl]-7H-pyrrolo[2,3-d]pyrimidin-4-yl]oxy]acetic acid as a solid. nmr (300 MHz, dmso-$d_6$) δ0.99 (t, 3H), 2.49 (s, 3H), 2.91 (q, 2H), 4.87 (s, 2H), 5.52 (s, 2H), 6.90 (d, 1H), 7.04 (d, 1H), 7.10 (dt, 1H), 7.36 (dt, 1H), 7.60 (br s, 1H), 8.02 (br s, 1H)

AR. Preparation of [[2-(methylthio)-5-(aminooxoacetyl)-6-ethyl-7- [[3-(trifluoromethyl)phenyl]methyl]-7H-pyrrolo[2,3-d]pyrimidin-4-yl]oxy]acetic Acid Methyl Ester

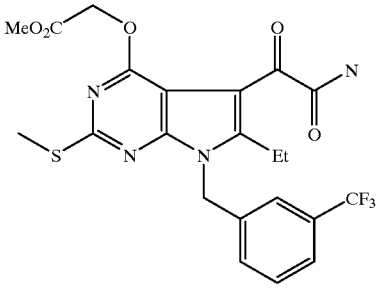

To a solution of 256 mg (0.582 mmol) of [[2-(methylthio)-6-ethyl-7-[[3-(trifluoromethyl)phenyl]methyl]-7H-pyrrolo[2,3-d]pyrimidin-4-yl]oxy]acetic acid methyl ester in 9 mL of chloroform was added 0.15 mL of oxalyl chloride followed by 0.07 mL of pyridine. The reaction stirred at ambient temperature and was monitored by nmr for conversion to product. Additional oxalyl chloride (0.200 mL) was added in portions over 3 days. The reaction was quenched into 4.0 mL of dilute ammonium hydroxide and the product was extracted into 4.0 mL of methylene chloride. The organic phase was washed with water, dried with sodium sulfate and concentrated to 420 mg of yellow solid. The residue was purified by flash chromatography (42 g of silica, ethyl acetate) to provide 66 mg (22%) of [[2-(methylthio)-5-(aminooxoacetyl)-6-ethyl-7-[[3-(trifluoromethyl)phenyl]-methyl]-7H-pyrrolo(2,3-d]pyrimidin-4-yl]oxy]acetic acid methyl ester as a solid. nmr (300 MHz, dmso-$d_6$) δ1.00 (t, 3H), 2.34 (s, 3H), 2.81 (q, 2H), 3.65 (s, 3H), 4.97 (s, 2H), 5.62 (s, 2H), 6.47 (d, 1H), 7.53 (m, 2H), 7.65 (s, 1H), 7.83 (d, 1H) , 8.06 (s, 1H)

AS. Preparation of [[2-(methylthio)-5-(aminooxoacetyl)-6-ethyl-7-[[3-(trifluoromethyl)phenyl]methyl]-7H-pyrrolo[2,3-d]pyrimidin-4-yl]oxy]acetic Acid

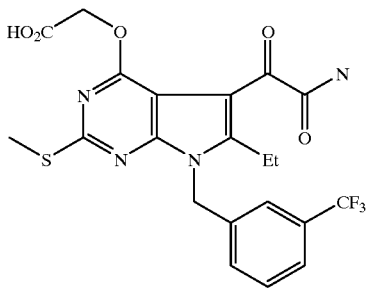

A mixture of 66 mg (0.129 mmol) of [[2-(methylthio)-5-(aminooxoacetyl)-6-ethyl-7-[[3-(trifluoromethyl)phenyl]methyl]-7H-pyrrolo[2,3-d]pyrimidin-4-yl]oxy]acetic acid methyl ester and 10 mL of methanol was treated with 0.10 mL of 2 M sodium hydroxide and stirred at reflux for 4 hours. The reaction was cooled to ambient temperature. The product precipitated upon addition of 1 M HCl and was collected by filtration. The solids were dried in vacuo to provide 50 mg (79%) of [[2-(methylthio)-5-(aminooxoacetyl)-6-ethyl-7-[[3-(trifluoromethyl)phenyl]methyl]-7H-pyrrolo[2,3-d]pyrimidin-4-yl]oxy]acetic acid as a solid. nmr (300 MHz, dmso-$d_6$) $\delta$0.99 (t, 3H), 2.36 (s, 3H), 2.82 (q, 2H), 4.86 (s, 2H), 5.62 (s, 2H), 6.48 (d, 1H), 7.51 (m, 2H), 7.64 (s, 1H), 7.84 (d 1H), 8.05 (s, 1H)

AT. Preparation of [[2-(methylthio)-5-(aminooxoacetyl)-6-ethyl-7-[(3-chlorophenyl)methyl]-7H-pyrrolo[2,3-d]pyrimidin-4-yl]oxy]acetic Acid Methyl Ester

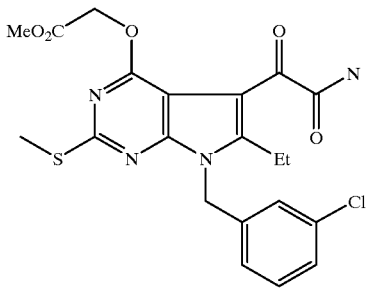

To a solution of 150 mg (0.371 mmol) of [[2-(methylthio)-6-ethyl-7-[(3-chlorophenyl)methyl]-7H-pyrrolo[2,3-d]pyrimidin-4-yl]oxy]acetic acid methyl ester in 5 mL of chloroform was added 0.10 mL of oxalyl chloride followed by 0.04 mL of pyridine. The reaction stirred at ambient temperature and was monitored by nmr for conversion to product. Additional oxalyl chloride (0.030 mL) was added after 24 hours. After 48 hours, the reaction was quenched into 4.0 mL of dilute ammonium hydroxide and the product was extracted into 5.0 mL of methylene chloride. The organic phase was washed with water, dried with sodium sulfate and concentrated to 400 mg of yellow solid. The residue was purified by flash chromatography (38 g of silica, ethyl acetate) to provide 109 mg (62%) of [[2-(methylthio)-5-(aminooxoacetyl)-6-ethyl-7-[(3-chlorophenyl)methyl]-7H-pyrrolo[2,3-d]pyrimidin-4-yl]oxy]acetic acid methyl ester as a solid. nmr (300 MHz, dmso-$d_6$) $\delta$1.00 (t, 3H), 2.45 (s, 3H), 2.90 (q, 2H), 3.65 (s, 3H), 4.97 (s, 2H), 5.52 (s, 2H), 7.01 (m, 1H), 7.31 (m, 3H), 7.60 (s, 1H), 8.02 (s, 1H)

AU. Preparation of [[2-(methylthio)-5-(aminooxoacetyl)-6-ethyl-7-[(3-chlorophenyl)methyl]-7H-pyrrolo[2,3-d]pyrimidin-4-yl]oxy]acetic Acid

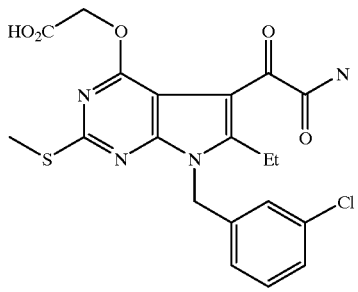

A mixture of 109 mg (0.228 mmol) of [[2-(methylthio)-5-(aminooxoacetyl)-6-ethyl-7-[(3-chlorophenyl)methyl]-7H-pyrrolo[2,3-d]pyrimidin-4-yl]oxy]acetic acid methyl ester and 10 mL of methanol was treated with 0.17 mL of 2 M sodium hydroxide and stirred at reflux for 3 hours. The reaction was cooled to ambient temperature and neutralized to pH 1 with 1 M HCl then concentrated to a solid. The solids were triturated with water and dried in vacuo to provide 99 mg (94%) of [[2-(methylthio)-5-(aminooxoacetyl)-6-ethyl-7-[(3-chlorophenyl)methyl]-7H-pyrrolo[2,3-d]pyrimidin-4-yl]oxy]acetic acid as a solid. nmr (300 MHz, dmso-$d_6$) $\delta$1.00 (t, 3H), 2.46 (s, 3H), 2.90 (q, 2H), 4.85 (s, 2H), 5.49 (s, 2H), 7.01 (m, 1H), 7.32 (m, 3H), 7.60 (s, 1H), 8.00 (s, 1H)

AV. Preparation of 2-(methylthio)-4-chloro-6-ethyl-7-[(3-chlorophenyl)methyl]-7H-pyrrolo[2,3-d]pyrimidine

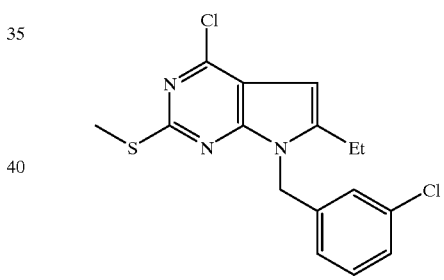

To a suspension of 48 mg (2.00 mmol) of sodium hydride in 4.0 mL of tetrahydrofuran was added 227 mg (1.00 mmol) of 2-(methylthio)-4-chloro-6-ethyl-1H-pyrrolo[2,3-d]pyrimidine and 410 mg (2.00 mmol) of 3-chlorobenzyl bromide. The reaction was stirred at ambient temperature for 18 hours then diluted with 30 mL of methylene chloride and washed with 20 mL of saturated sodium bicarbonate solution. The organic phase was dried with sodium sulfate and concentrated. The crude product was purified by flash chromatography (25 g silica, methylene chloride-heptane gradient 1:1 to 100:0) to provide 350 mg (99%) of 2-(methylthio)-4-chloro-6-ethyl-7-[(3-chlorophenyl)methyl]-7H-pyrrolo[2,3-d]pyrimidine as a white solid. nmr (500 MHz, CDCl$_3$) $\delta$1.33 (t, J=7.4 Hz, 3H), 2.58 (s, 3H), 2.59 (q, J=7.4 Hz, 2H), 5.30 (s, 2H), 6.29 (s, 1H), 6.92 (d, J=7.4 Hz, 1H), 7.09 (s, 1H), 7.23 (m, 2H)

AW. Preparation of [[2-(methylthio)-6-ethyl-7-[(3-chlorophenyl)methyl]-7H-pyrrolo[2,3-d]pyrimidin-4-yl]oxy]acetic Acid Methyl Ester

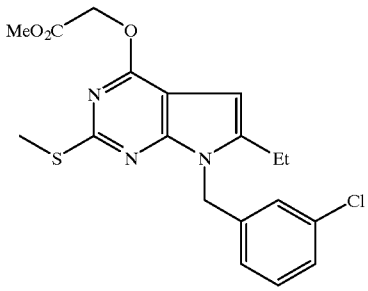

To a suspension of 79 mg (3.30 mmol) of sodium hydride in 2 mL of benzene was added 225 mg (2.75 mmol) of methyl glycolate and a solution of 320 mg (0.91 mmol) of 2-(methylthio)-4-chloro-6-ethyl-7-[(3-chlorophenyl) methyl]-7H-pyrrolo[2,3-d]pyrimidine in 2 ml of benzene. The mixture was then heated at 60° C. After 24 hours the reaction was cooled to ambient temperature and an additional 40 mg of sodium hydride and 110 mg of methyl glycolate were added. After 3 days, the reaction was partitioned by the addition of 2 mL of 2 M sodium hydrogen sulfate and 20 mL of ethyl acetate. The organic phase was washed with 10 mL of water, dried with sodium sulfate and concentrated. The product was purified by flash chromatography (30 g silica, methylene chloride-heptane gradient 2:1 to 100:0) to provide 200 mg (54%) of [[2-(methylthio)-6-ethyl-7-[(3-chlorophenyl)methyl]-7H-pyrrolo[2,3-d] pyrimidin-4-yl]oxy]acetic acid methyl ester as a white solid. nmr (500 MHz, CDCl$_3$) δ1.26 (t, J=7.4 Hz, 3H), 2.53 (s, 3H), 2.56 (q, J=7.4 Hz, 2H), 3.79 (s, 3H), 5.05 (s, 2H), 5.35 (s, 2H), 6.31 (s, 1H), 6.92 (d, J=6.7 Hz, 1H), 7.08 (s, 1H), 7.21 (m, 2H)

AX. Preparation of [[6-ethyl-7-[(3-chlorophenyl)methyl]-7H-pyrrolo[2,3-d]pyrimidin-4-yl]oxy]acetic Acid Methyl Ester

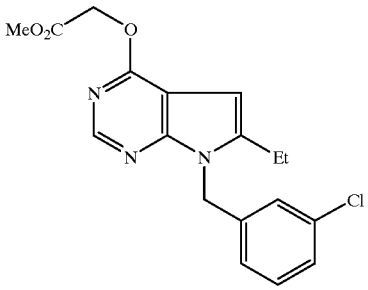

A solution of 186 mg (0.458 mmol) of [[2-(methylthio)-6-ethyl-7-[(3-chlorophenyl)methyl]-7H-pyrrolo[2,3-d] pyrimidin-4-yl]oxy]acetic acid methyl ester in 4 mL of ethyl acetate and 1 mL of methanol was heated to reflux and treated with 1.05 g of Raney Ni in portions over 3 hours. The reaction was diluted with 2 mL of methylene chloride and the solids were removed by filtration through a filter aid. The reaction mixture was dried with sodium sulfate and concentrated to provide 140 mg (85%) of [[6-ethyl-7-[(3-chlorophenyl)methyl]-7H-pyrrolo[2,3-d]pyrimidin-4-yl] oxy]acetic acid methyl ester as a solid. nmr (500 MHz, CDCl$_3$) δ1.29 (t, J=7.4 Hz, 3H), 2.62 (q, J=7.4 Hz, 2H), 3.80 (s, 3H), 5.09 (s, 2H), 5.42 (s, 2H), 6.41 (s, 1H), 6.88 (d, J=6.9 Hz, 1H),. 7.04 (s, 1H), 7.21 (m, 2H), 8.38 (s, 1H)

AY. Preparation of [[5-(aminooxoacetyl)-6-ethyl-7-[(3-chlorophenyl)methyl]-7H-pyrrolo[2,3-d]pyrimidin-4-yl] oxy]acetic Acid Methyl Ester

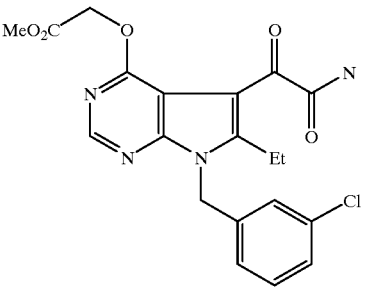

To a suspension of 110 mg (0.30 mmol) of [[6-ethyl-7-[(3-chlorophenyl)methyl]-7H-pyrrolo[2,3-d]pyrimidin-4-yl]oxy]acetic acid methyl ester in 3 mL of chloroform was added 0.106 mL of oxalyl chloride followed by 0.10 mL of pyridine. The reaction was stirred for 48 hours at ambient temperature then an additional 0.100 mL of oxalyl chloride and 0.100 mL of pyridine was added. This mixture was stirred and additional 4 days then quenched into solution prepared from 4 mL of water and 2 mL of concentrated ammonium hydroxide. The mixture was partitioned by the addition of 20 mL of ethyl acetate and 10 mL of water. The organic phase was dried with sodium sulfate and concentrated to 91 mg of crude solid. The residue was purified by flash chromatography (7 g of silica, ethyl acetate) to provide 69 mg (53%) of [[5-(aminooxoacetyl)-6-ethyl-7-[(3-chlorophenyl)methyl]-7H-pyrrolo[2,3-d]pyrimidin-4-yl] oxy]acetic acid methyl ester as a white solid. nmr (500 MHz, CDCl$_3$) δ1.15 (t, J=7.4 Hz, 3H), 2.95 (q, J=7.4 Hz, 2H), 3.78 (s, 3H), 5.05 (s, 2H), 5.50 (s, 2H), 5.68 (br s, 1H), 6.60 (br s, 1H), 6.98 (d, J=7.4 Hz, 1H), 7.2 (s, 1H), 7.26 (m, 2H), 8.46 (s, 1H)

AZ. Preparation of [[5-(aminooxoacetyl)-6-ethyl-7-[(3-chlorophenyl)methyl]-7H-pyrrolo[2,3-d]pyrimidin-4-yl] oxy]acetic Acid

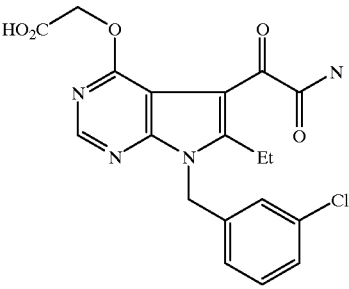

A mixture of 67 mg (0.15 mmol) of [[5-(aminooxoacetyl)-6-ethyl-7-[(3-chlorophenyl)methyl]-7H-pyrrolo[2,3-d] pyrimidin-4-yl]oxy]acetic acid methyl ester and 2 mL of methanol were treated with 0.15 mL of 2 M sodium hydroxide and stirred at ambient temperature for 3 days. The reaction was concentrated to an oil then diluted with 5 mL of water. The product precipitated upon the addition of 0.45 mL of 1 M HCl to provide 59 mg (95%) of [[5-(aminooxoacetyl)-6-ethyl-7-[(3-chlorophenyl)methyl]-7H-pyrrolo[2,3-d]pyrimidin-4-yl]oxy]acetic acid as a white solid. nmr (500 MHz, dmso-d$_6$) δ1.01 (t, J=7.4 Hz, 3H), 2.95 (q, J=7.4 Hz, 2H), 4.92 (s, 2H), 5.60 (s, 2H), 7.03 (d, J=7.4 Hz, 1H), 7.26 (s, 1H), 7.34 (m, 2H), 7.58 (br s, 1H), 8.00 (br s, 1H), 8.46 (s, 1H), 12.9 (br s, 1H)

BA. Preparation of 2-(methylthio)-4-chloro-6-ethyl-7-[[3-(trifluoromethyl)phenyl]methyl]-7H-pyrrolo[2,3-d]pyrimidine

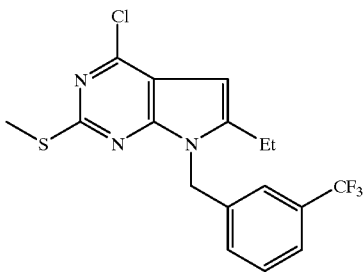

To a suspension of 48 mg (2.00 mmol) of sodium hydride in 4.0 mL of tetrahydrofuran was added 227 mg (1.00 mmol) of 2-(methylthio)-4-chloro-6-ethyl-1H-pyrrolo[2,3-d]pyrimidine and 478 mg (2.00 mmol) of 3-(trifluoromethyl) benzyl bromide. The reaction was stirred at ambient temperature for 18 hours then diluted with 30 mL of methylene chloride and washed with 20 mL of saturated sodium bicarbonate solution. The organic phase was dried with sodium sulfate and concentrated. The crude product was purified by flash chromatography (25 g silica, methylene chloride-heptane gradient 1:1 to 100:0) to provide 320 mg (83%) of 2-(methylthio)-4-chloro-6-ethyl-7-[[3-(trifluoromethyl)-phenyl]methyl]-7H-pyrrolo[2,3-d]pyrimidine as a white solid. nmr (500 MHz, CDCl$_3$) δ1.31 (t, J=7.3 Hz, 3H), 2.58 (s, 3H), 2.59 (q, J=7.3 Hz, 2H), 5.44 (s, 2H), 6.31 (s, 1H), 7.18 (d, J=7.8 Hz, 1H), 7.41 (t, J=7.8 Hz, 1H), 7.45 (s, 1H), 7.54 (d, J=7.8 Hz, 1H)

BB. Preparation of [[2-(methylthio)-6-ethyl-7-[[3-(trifluoromethyl)phenyl]methyl]-7H-pyrrolo[2,3-d]pyrimidin-4-yl]oxy]acetic Acid Methyl Ester

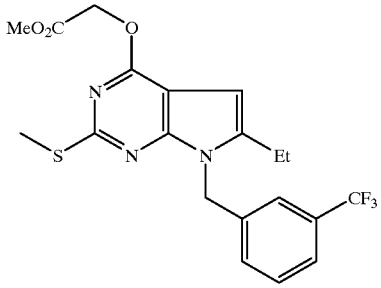

To a suspension of 72 mg (3.00 mmol) of sodium hydride in 2 mL of benzene was added 225 mg (2.49 mmol) of methyl glycolate and a solution of 300 mg (0.78 mmol) of 2-(methylthio)-4-chloro-6-ethyl-7-[[3-(trifluoromethyl)-phenyl]methyl]-7H-pyrrolo[2,3-d]pyrimidine in 2 ml of benzene. The mixture was then heated at 60° C. After 24 hours the reaction was cooled to ambient temperature and an additional 36 mg of sodium hydride and 110 mg of methyl glycolate were added. After 3 days, the reaction was partitioned by the addition of 2 mL of 2 M sodium hydrogen sulfate and 20 mL of ethyl acetate. The organic phase was washed with 10 mL of water, dried with sodium sulfate and concentrated. The product was purified by flash chromatography (30 g silica, methylene chloride-heptane gradient 2:1 to 100:0) to provide 187 mg (54%) of [[2-(methylthio)-6-ethyl-7-[[3-(trifluoromethyl)phenyl]methyl]-7H-pyrrolo[2,3-d]pyrimidin-4-yl]oxy]acetic acid methyl ester as a white solid. nmr (500 MHz, CDCl$_3$) δ1.26 (t, J=7.4 Hz, 3H), 2.52 (s, 3H), 2.56 (q, J=7.4 Hz, 2H), 3.79 (s, 3H),5.05 (s, 2H), 5.42 (s, 2H), 6.32 (s, 1H), 7.18 (d, J=7.8 Hz, 1H), 7.39 (t, J=7.8 Hz, 1H), 7.44 (s, 1H), 7.51 (d, J=7.8 Hz, 1H)

BC. Preparation of [[6-ethyl-7-[[3-(trifluoromethyl)phenyl]methyl]-7H-pyrrolo[2,3-d]pyrimidin-4-yl]oxy]acetic Acid Methyl Ester

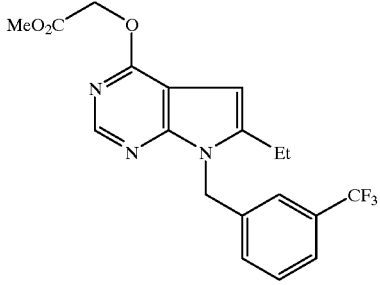

A solution of 173 mg (0.394 mmol) of [[2-(methylthio)-6-ethyl-7-[[3-(trifluoromethyl)phenyl]methyl]-7H-pyrrolo[2,3-d]pyrimidin-4-yl]oxy]acetic acid methyl ester in 5 mL of ethyl acetate and 1 mL of methanol was heated to reflux and treated with 1.05 g of Raney Ni in portions over 3 hours. The reaction was diluted with 2 mL of methylene chloride and the solids were removed by filtration through a filter aid. The reaction mixture was dried with sodium sulfate and concentrated to provide 128 mg (83%) of [[6-ethyl-7-[[3-(trifluoromethyl)phenyl]methyl]-7H-pyrrolo[2,3-d]pyrimidin-4-yl]oxy]acetic acid methyl ester as a solid. nmr (500 MHz, CDCl$_3$) δ1.29 (t, J=7.4 Hz, 3H), 2.63 (q, J=7.4 Hz, 2H), 3.80 (s, 3H), 5.10 (s, 2H), 5.51 (s, 2H), 6.43 (s, 1H), 7.14 (d, J=7.7 Hz, 1H), 7.38 (m, 1H), 7.44 (s, 1H), 7.51 (d, J=7.7 Hz, 1H), 8.38 (s, 1H)

BD. Preparation of [[5-(aminooxoacetyl)-6-ethyl-7-[[3-(trifluoromethyl)phenyl]methyl]-7H-pyrrolo[2,3-d]pyrimidin-4-yl]oxy]acetic Acid Methyl Ester

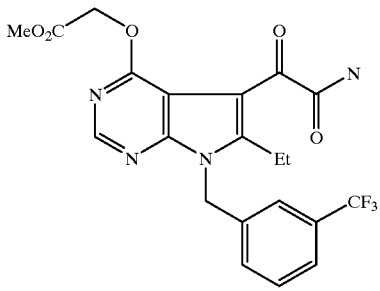

To a suspension of 115 mg (0.29 mmol) of [[6-ethyl-7-[[3-(trifluoromethyl)phenyl]methyl]-7H-pyrrolo[2,3-d]pyrimidin-4-yl]oxy]acetic acid methyl ester in 3 mL of chloroform was added 0.102 mL of oxalyl chloride followed by 0.094 mL of pyridine. The reaction was stirred for 48 hours at ambient temperature then an additional 0.100 mL of oxalyl chloride and 0.100 mL of pyridine was added. This mixture was stirred and additional 4 days then quenched into solution prepared from 4 mL of water and 2 mL of concentrated ammonium hydroxide. The mixture was partitioned by the addition of 20 mL of ethyl acetate and 10 mL of water. The organic phase was dried with sodium sulfate and concentrated to 108 mg of crude solid. The residue was purified by flash chromatography (7 g of silica, ethyl acetate) to provide 72 mg (53%) of [[5-(aminooxoacetyl)-6-ethyl-7-

[[3-(trifluoromethyl)phenyl]-methyl]-7H-pyrrolo[2,3-d]pyrimidin-4-yl]oxy]acetic acid methyl ester as a white solid. nmr (500 MHz, CDCl₃) δ1.15 (t, J=7.5 Hz, 3H), 2.96 (q, J=7.5 Hz, 2H), 3.78 (s, 3H), 5.07 (s, 2H), 5.57 (s, 2H), 5.68 (br s, 1H), 6.60 (br s, 1H), 7.24 (d, J=7.8 Hz, 1H), 7.40 (d, J=7.8 Hz, 1H), 7.54 (s, 1H), 7.55 (d, J=7.8 Hz, 1H), 8.46 (s, 1H)

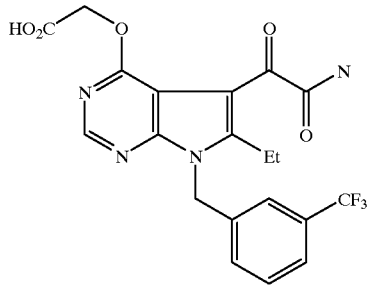

A mixture of 70 mg (0.15 mmol) of [[5-(aminooxoacetyl)-6-ethyl-7-[[3-(trifluoromethyl)phenyl]methyl]-7H-pyrrolo[2,3-d]pyrimidin-4-yl]oxy]acetic acid methyl ester and 2 mL of methanol were treated with 0.15 mL of 2 M sodium hydroxide and stirred at ambient temperature for 3 days. The reaction was concentrated to an oil then diluted with 5 mL of water. The product precipitated upon the addition of 0.45 mL of 1 M HCl to provide 60 mg (90%) of [[5-(aminooxoacetyl)-6-ethyl-7-[[3-(trifluoromethyl)phenyl]methyl]-7H-pyrrolo[2,3-d]pyrimidin-4-yl]oxy]acetic acid as a white solid. nmr (500 MHz, dmso-d₆) δ1.00 (t, J=7.4 Hz, 3H), 2.98 (q, J=7.4 Hz, 2H), 4.92 (s, 2H), 5.70 (s, 2H), 7.31 (d, J=7.8 Hz, 1H), 7.53 (t, J=7.8 Hz, 1H) 7.58 (br s, 1H), 7.65 (m, 2H), 8.00 (br s, 1H), 8.46 (s, 1H)

BDA. Preparation of [[2-(methylthio)-5-(aminooxoacetyl)-6-ethyl-7-[[2-(trifluoromethyl)phenyl]methyl]-7H-pyrrolo[2,3-d]pyrimidin-4-yl]oxy]acetic Acid Methyl Ester

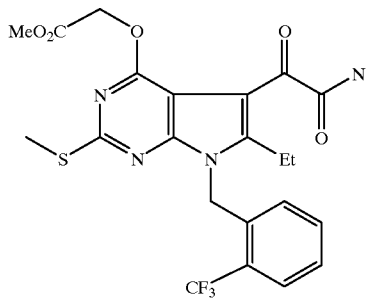

To a solution of 256 mg (0.582 mmol) of [[2-(methylthio)-6-ethyl-7-[[2-(trifluoromethyl)phenyl]methyl]-7H-pyrrolo[2,3-d]pyrimidin-4-yl]oxy]acetic acid methyl ester in 9 mL of chloroform was added 0.15 mL of oxalyl chloride followed by 0.07 mL of pyridine. The reaction was stirred at ambient temperature and was monitored by nmr for conversion to product. Additional oxalyl chloride (0.200 mL) was added in portions over 3 days. The reaction was quenched into 4.0 mL of dilute ammonium hydroxide and the product was extracted into 4.0 mL of methylene chloride. The organic phase was washed with water, dried with sodium sulfate and concentrated to 420 mg of yellow solid. The residue was purified by flash chromatography (42 g of silica, ethyl acetate) to provide 66 mg (22%) of [[2-(methylthio)-5-(aminooxoacetyl)-6-ethyl-7-[[2-(trifluoromethyl)phenyl]methyl]-7H-pyrrolo[2,3-d]pyrimidin-4-yl]oxy]acetic acid methyl ester as a solid. nmr (300 MHz, dmso-d₆) δ1.00 (t,3H), 2.34 (s,3H), 2.81 (q,2H), 3.65 (s,3H), 4.97 (s,2H), 5.62 (s,2H), 6.47 (d, 1H), 7.53 (m,2H), 7.65(s, 1H), 7.83 (d, 1H), 806 (s, 1H)

BDB. Preparation of [[2-(methylthio)-5-(aminooxoacetyl)-6-ethyl-7-[[2-(trifluoromethyl)phenyl]methyl]-7H-pyrrolo[2,3-d]pyrimidin-4-yl]oxy]acetic Acid

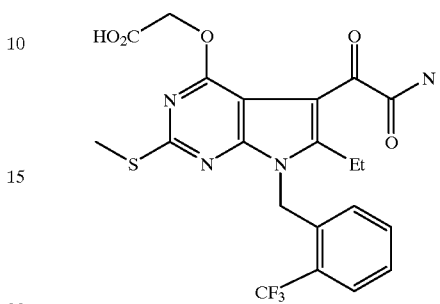

A mixture of 66 mg (0.129 mmol) of [[2-(methylthio)-5-(aminooxoacetyl)-6-ethyl-7-[[2-(trifluoromethyl)phenyl]methyl]-7H-pyrrolo[2,3-d]pyrimidin-4-yl]oxy)acetic acid methyl ester and 10 mL of methanol was treated with 0.10 mL of 2M sodium hydroxide and stirred at reflux for 4 hours. The reaction was cooled to ambient temperature. The product precipitated upon addition of 1MHCland was collected by filtration. The solids were dried in vacuo to provide 50 mg (79%) of [[2-(methylthio)-5-(aminooxoacetyl)-6-ethyl-7-[[2-(trifluoromethyl)phenyl]methyl]-7H-pyrrolo[2,3-d]pyrimidin-4-yl]oxy]acetic acid as a solid. nmr(300 MHz, dmso-d₆) δ0.99 (t,3H), 2.36 (s,3H), 2.82 (q,2H), 4.86 (s,2H), 5.62 (s,2H), 6.48 (d, 1H), 751 (m,2H),7.64 (s, 1H), 7.84 (d 1H), 8.05 (s, 1H)

Assay

The following chromogenic assay procedure was used to identify and evaluate inhibitors of recombinant human secreted phospholipase A₂. The assay described herein has been adapted for high volume screening using 96 well microtiter plates. A general description of this assay method is found in the article, "Analysis of Human Synovial Fluid Phospholipase A₂ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference): Reagents:

Reaction Buffer

| | |
|---|---|
| CaCl₂.2H₂O | (1.47 g/L) |
| KCl | (7.455 g/L) |

Bovine Serum Albumin (fatty acid free) (1 g/L)
(Sigma A-7030, product of Sigma Chemical Co. St. Louis Mo., USA)

| | |
|---|---|
| TRIS HCl | (3.94 g/L) | pH 7.5 (adjust with NaOH)
Enzyme Buffer 0.05 NaOAc.3H2O, pH 4.5

0.2 NaCl

Adjust pH to 4.5 with acetic acid

DTNB—5,5'-dithiobis-2-nitrobenzoic acid

Racemic Diheptanoyl Thio-PC racemic 1,2-bis(heptanoylthio)-1,2-dideoxy-sn-glycero-3-phosphorylcholine TRITON X-100™ prepare at 6.249 mg/ml in reaction buffer to equal 10 uM.

Reaction Mixture

A measured volume of racemic dipheptanoyl thio PC supplied in chloroform at a concentration of 100 mg/ml is taken to dryness and redissolved in 10 millimolar TRITON X-100™ nonionic detergent aqueous solution.

Reaction Buffer is added to the solution, then DTNB to give the Reaction Mixture.

The reaction mixture thus obtained contains lmM diheptanoly thio-PC substrate, 0.29 mm Triton X-100™ detergent, and 0.12 mm DTMB in a buffered aqueous solution at pH 7.5.

Assay Procedure:

1. Add 0.2 ml reaction mixture to all wells;
2. Add 10 ul test compound (or solvent blank) to appropriate wells, mix 20 seconds;
3. Add 50 nanograms of sPLA$_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, IC$_{50}$ values were determined. Typically, the IC$_{50}$ values (see, Table I, below) were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of IC$_{50}$ values. IC$_{50}$ were determined by plotting log concentration versus inhibition values in the range from 10–90% inhibition.

Results of Human Secreted Phospholipase A$_2$ Inhibition Tests Using pyrrolo[2,3-d]pyrimidines

TABLE 1

Human Recombinant hnp-sPLA$_2$ Chromogenic Assay IC$_{50}$ Table

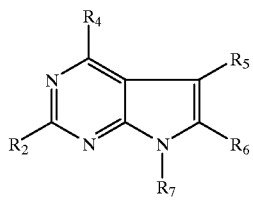

| $R_4'$ | $R_2'$ | $R_{71}$ | IC$_{50}$ (micromolar) n = 3 – 4 (ave) |
|---|---|---|---|
| —CH$_3$ | —CH$_3$ | phenyl | 4.654 |
| —CH$_3$ | —H | phenyl | 5.463 |
| —H | —CH$_3$ | phenyl | 0.088 |
| —H | —H | phenyl | 0.048 |
| —H | —SCH$_3$ | phenyl | 0.019 |
| —H | —S-phenyl | phenyl | 0.011 |
| —H | —O—CH$_3$ | phenyl | 0.046 |
| —H | —S-methyl | m-F-phenyl | 0.016 |
| —H | —S-methyl | m-Cl-phenyl | 0.019 |
| —H | —S-methyl | o-phenyl-phenyl | 0.009 |
| —H | —S-methyl | m-CF$_3$-phenyl | 0.013 |
| —H | —H | o-phenyl-phenyl | 0.114 |
| —H | —H | m-Cl-phenyl | 0.091 |
| —H | —H | m-CF$_3$-phenyl | 0.124 |
| —H | —H | m-F-phenyl | 0.098 |

While the present invention has been illustrated above by certain specific embodiments, it is not intended that these specific examples should limit the scope of the invention as described in the appended claims.

We claim:

1. A compound represented by the formula (I), or a pharmaceutically acceptable salt, solvate, or ester prodrug wherein said ester is methyl, ethyl, propyl, isopropyl, n-butyl, isobutyl, tert-butyl, morpholinoethyl, or N,N-diethylglycolamido;

(I)

wherein

R$_2$ is selected from hydrogen, non-interfering substituent, carbocyclic radical, carbocyclic radical substituted with non-interfering substituent(s), heterocyclic radical, and heterocyclic radical substituted with non-interfering substituent(s);

R$_4$ is —(L$_4$)—(acidic group); wherein —(L$_4$)—, is a divalent acid linker having an acid linker length of 1 to 4;

R$_5$ is —(L$_5$)—Z, where —(L$_5$)— is a divalent linker group selected from a bond or a divalent group selected from:

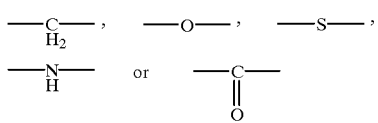

and Z is selected from a group represented by the formulae,

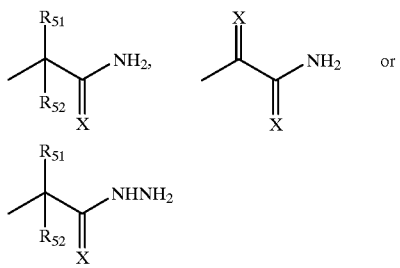

where $R_{51}$ and $R_{52}$ are independently selected from hydrogen, $C_1-C_8$ alkyl, $C_1-C_8$ haloalkyl, and $C_3-C_4$ cycloalkyl, and X is oxygen or sulfur;

$R_6$ is hydrogen, or a group containing 1 to 4 non-hydrogen atoms plus any required hydrogen atoms;

$R_7$ is selected from groups (a), (b) and (c) wherein;
(a) is $C_7-C_{20}$ alkyl, $C_7-C_{20}$ haloalkyl, $C_7-C_{20}$ alkenyl, $C_7-C_{20}$ alkynyl, carbocyclic radical, or heterocyclic radical, or
(b) is a member of (a) substituted with one or more independently selected non-interfering substituents; or
(c) is the group $-(L_7)-R_{71}$; where, $-(L_7)-$ is a divalent linking group of 1 to 12 atoms selected from carbon, hydrogen, oxygen, nitrogen, and sulfur; wherein the combination of atoms in $-(L_7)-$ is selected from the group consisting of (i) carbon and hydrogen only, (ii) sulfur only, (iii) oxygen only, (iv) nitrogen and hydrogen only, (v) carbon, hydrogen, and sulfur only, and (vi) and carbon, hydrogen, and oxygen only; and where $R_{71}$ is a group selected from (a) or (b);

provided that the heterocyclic radical is pyrrolyl, pyrrolodinyl, piperidinyl, furanyl, thiophenyl, pyrazolyl, imidazolyl, phenylimidazolyl, triazolyl, isoxazolyl, oxazolyl, thiazolyl, thiadiazolyl, indolyl, carbazolyl, norharmanyl, azaindolyl, benzofuranyl, dibenzofuranyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pyridinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, morpholino, thiomorpholino, homopiperazinyl, tetrahydrofuranyl, tetrahydropyranyl, oxacanyl, 1,3-dioxolanyl, 1,3-dioxanyl, 1,4-dioxanyl, tetrahydrothiopheneyl, pentamethylenesulfadyl, 1,3-dithianyl, 1,4-dithianyl, 1,4-thioxanyl, azetidinyl, hexamethyleneiminium, heptamethyleneiminium, piperazinyl or quinoxalinyl;

provided that the carbocyclic radical is cycloalkyl, cycloalkenyl, phenyl, thiophenyl, naphthyl, norbornanyl, bicycloheptadienyl, tolulyl, xylenyl, indenyl, stilbenyl, terphenylyl, diphenylethylenyl, phenyl-cyclohexenyl, acenaphthylenyl, and anthracenyl, biphenyl, bibenzylyl or related bibenzylyl homologues represented by the formula (a):

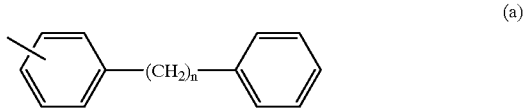

where
n is a number from 1 to 8;
provided that the non-interfering radical is $C_1-C_8$ alkyl, $C_2-C_8$ alkenyl, $C_2-C_8$ alkynyl, $C_7-C_{12}$ aralkyl, $C_7-C_{12}$ alkaryl, $C_3-C_8$ cycloalkyl, $C_3-C_8$ cycloalkenyl, phenyl, tolulyl, xylenyl, biphenyl, $C_1-C_8$ alkoxy, $C_2-C_8$ alkenyloxy, $C_2-C_8$ alkynyloxy, $C_2-C_{12}$ alkoxyalkyl, $C_2-C_{12}$ alkoxyalkyloxy, $C_2-C_{12}$ alkylcarbonyl, $C_2-C_{12}$ alkylcarbonylamino, $C_1-C_{12}$ alkoxyamino, $C_2-C_{12}$ alkoxyaminocarbonyl, $C_1-C_{12}$ alkylamino, $C_1-C_8$ alkylthio, $C_2-C_{12}$ alkylthiocarbonyl, $C_1-C_{12}$ alkylsulfinyl, $C_1-C_8$ alkylsulfonyl, $C_1-C_8$ haloalkoxy, $C_1-C_8$ haloalkylsulfonyl, $C_1-C_8$ haloalkyl, $C_1-C_8$ hydroxyalkyl, $-C(O)O(C_1-C_8$ alkyl$)$, $-(CH_2)_n-O-(C_1-C_8$ alkyl$)$, benzyloxy, phenoxy, phenylthio, $-(CONHSO_2R)$, $-CHO$, amino, amidino, bromo, carbamyl, carboxyl, carbalkoxy, $-(CH_2)_n-CO_2H$, chloro, cyano, cyanoguanidinyl, fluoro, guanidino, hydrazide, hydrazino, hydrazido, hydroxy, hydroxyamino, iodo, nitro, phosphono, $-SO_3H$, thioacetal, thiocarbonyl, or $C_1-C_8$ carbonyl; where n is from 1 to 8;

provided that the divalent acid linker $-(L_4)-$ for $R_4$ is a group represented by the formulae:

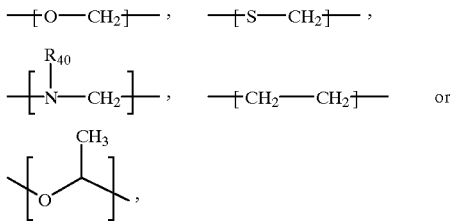

where
$R_{40}$ is hydrogen or $C_1-C_8$ alkyl; provided that the (acidic group) in $R_4$ is -5-tetrazolyl,

—SO$_3$H,

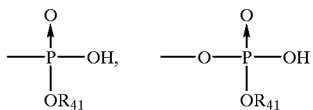

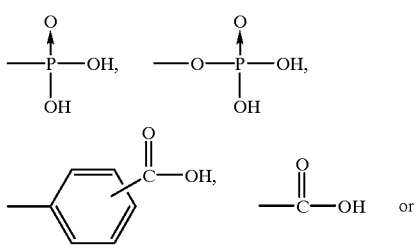

-continued

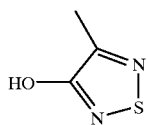

where

R$_{41}$ is a metal or C$_1$–C$_8$ alkyl; and
provided that R$_6$ is hydrogen, methyl, ethyl, propyl, isopropyl, cyclopropyl, C$_1$–C$_3$ alkoxy, C$_1$–C$_3$ alkylthio, C$_1$–C$_3$ haloalkyl, C$_1$–C$_3$ hydroxyalkyl or halo;
provided that the divalent linking group —(L$_7$)— is for R$_7$ is represented by the formulae (VIIa), (VIIb), (VIIc), (VIId), (VIIe), and (VIIf):

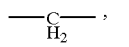 (VIIa)

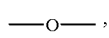 (VIIb)

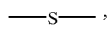 (VIIc)

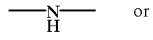 (VIId)

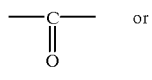 (VIIe)

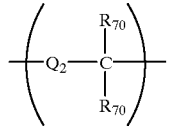 (VIIf)

where Q$_2$ is a bond or any of the divalent groups VIIa, VIIb, VIIc, VIId, and VIIe and each R$_{70}$ is independently hydrogen, C$_1$–C$_6$ alkyl, C$_1$–C$_6$ haloalkyl or C$_1$–C$_6$ alkoxy.

2. The compound of claim 1 wherein R$_2$ is selected from the group consisting of hydrogen, cyclopropyl, C$_1$–C$_8$ alkyl, C$_1$–C$_8$ haloalkyl, C$_1$–C$_8$ alkoxy, C$_1$–C$_8$ thioalkyl, C$_1$–C$_8$ alkylsulfonyl, phenyl, thiophenyl, and C$_1$–C$_{12}$ alkylamino.

3. The compound of claim 1 wherein the (acidic group) is —CO$_2$H.

4. The compound of claim 1 wherein for R$_5$ all X's are oxygen.

5. The compound of claim 1 wherein for R$_5$, Z is the group represented by the formula;

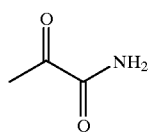

and the linking group —(L$_5$)— is a bond.

6. The compound of claim 1 wherein the linking group —(L$_7$)— of R$_7$ is —(CH$_2$)— or —(CH$_2$—CH$_2$)—.

7. The compound of claim 1 wherein for R$_7$ the combined group —(L$_7$)—R$_{71}$ is selected from the groups;

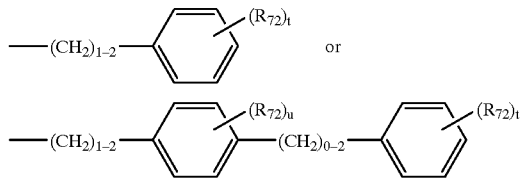

where R$_{72}$ is independently halo, C$_1$–C$_{10}$ alkyl, C$_1$–C$_{10}$ alkoxy, —S—(C$_1$–C$_{10}$ alkyl), C$_1$–C$_{10}$ haloalkyl, or C$_1$–C$_{10}$ hydroxyalkyl; t is a number from 0 to 5, and u is a number from 0 to 4.

8. The compound of claim 1 in the form of a sodium salt.

9. A compound represented by the formula (II), or a pharmaceutically acceptable salt, solvate, or ester prodrug derivative thereof; wherein said ester is methyl, ethyl, propyl, isopropyl, n-butyl, isobutyl, tert-butyl, morpholinoethyl, or N,N-diethylglycolamido;

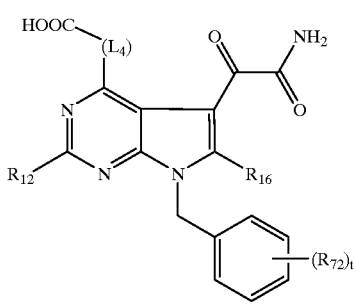 (II)

wherein;

R$_{12}$ is selected are hydrogen, methyl, ethyl, propyl, isopropyl, —S—CH$_3$, —S—C$_2$H$_5$, methylsulfonyl, ethylsulfonyl, thiophenyl, dimethylamino, diethylamino, ethylamino, methoxy, and ethoxy;

—(L4)— is a divalent group selected from

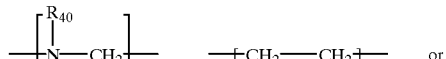

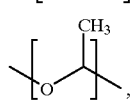

where

R$_{40}$ is hydrogen or C$_1$–C$_8$ alkyl.

R$_{16}$ is selected from hydrogen, methyl, ethyl, propyl, cyclopropyl, trifluoromethyl, thiomethyl, and halo; and R$_{72}$ is C$_1$–C$_8$ alkyl, C$_1$–C$_8$ alkoxy, —S—(C$_1$–C$_8$ alkyl), C$_1$–C$_8$ haloalkyl, C$_1$–C$_8$ hydroxyalkyl, and halo; and t is an integer from 0 to 5.

10. A compound selected from the group consisting of compounds represented by the formulae (C1), (C2), (C3), (C4) and (C5):

(C1)
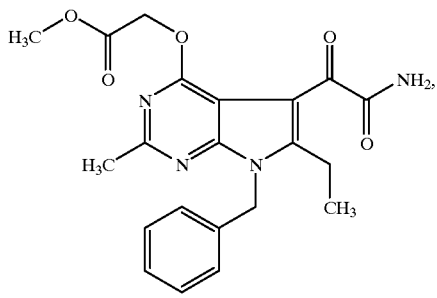

(C2)
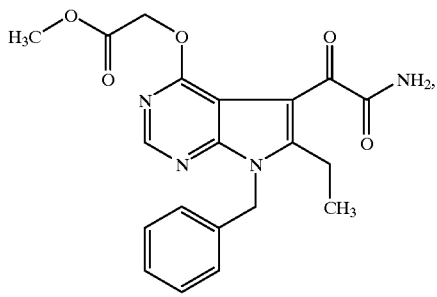

(C3)
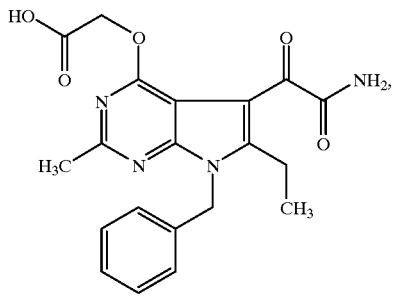

(C4)
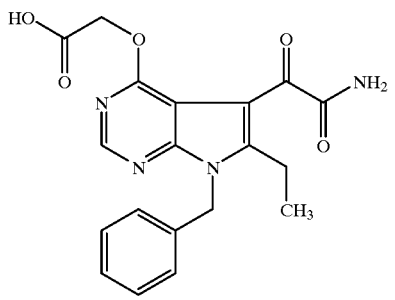

and (C5)
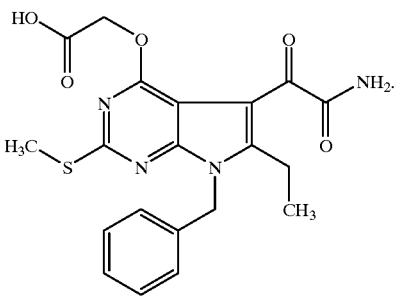

11. A compound selected from the group consisting of:

[[2-(methylthio)-5-(aminooxoacetyl)-6-ethyl-7-(phenylmethyl)-7H-pyrrolo[2,3-d]pyrimidin-4-yl]oxy] acetic acid methyl ester,

[[2-(phenylthio)-5-(aminooxoacetyl)-6-ethyl-7-(phenylmethyl)-7H-pyrrolo[2,3-d]pyrimidin-4-yl]oxy] acetic acid methyl ester,

[[2-(phenylthio)-5-(aminooxoacetyl)-6-ethyl-7-(phenylmethyl)-7H-pyrrolo[2,3-d]pyrimidin-4-yl]oxy] acetic acid,

[[2-methoxy-5-(aminooxoacetyl)-6-ethyl-7-(phenylmethyl)-7H-pyrrolo[2,3-d]pyrimidin-4-yl]oxy] acetic acid methyl ester,

[[2-methoxy-5-(aminooxoacetyl)-6-ethyl-7-(phenylmethyl)-7H-pyrrolo(2,3-d]pyrimidin-4-yl]oxy] acetic acid,

[[5-(aminooxoacetyl)-6-ethyl-7-([1,1'-biphenyl]-2-ylmethyl)-7H-pyrrolo[2,3-d]pyrimidin-4-yl]oxy]acetic acid methyl ester,

[[5-(aminooxoacetyl)-6-ethyl-7-([1,1'-biphenyl]-2-ylmethyl)-7H-pyrrolo[2,3-d]pyrimidin-4-yl]oxy]acetic acid,

[[5-(aminooxoacetyl)-6-ethyl-7-[(3-fluorophenyl)methyl]-7H-pyrrolo[2,3-d]pyrimidin-4-yl]oxy]acetic acid methyl ester,

[[5-(aminooxoacetyl)-6-ethyl-7-[(3-fluorophenyl)methyl]-7H-pyrrolo[2,3-d]pyrimidin-4-yl]oxy]acetic acid,

[[2-(methylthio)-5-(aminooxoacetyl)-6-ethyl-7-([1,1'-biphenyl]-2-ylmethyl)-7H-pyrrolo[2,3-d]pyrimidin-4-yl]oxy]acetic acid methyl ester,

[[2-(methylthio)-5-(aminooxoacetyl)-6-ethyl-7-([1,1'-biphenyl]-2-ylmethyl)-7H-pyrrolo[2,3-d]pyrimidin-4-yl]oxy]acetic acid,

[[2-(methylthio)-5-(aminooxoacetyl)-6-ethyl-7-[(3-fluorophenyl)methyl]-7H-pyrrolo[2,3-d]pyrimidin-4-yl]oxy]acetic acid methyl ester,

[[2-(methylthio)-5-(aminooxoacetyl)-6-ethyl-7-[(3-fluorophenyl)methyl]-7H-pyrrolo[2,3-d]pyrimidin-4-yl]oxy]acetic acid,

[[2-(methylthio)-5-(aminooxoacetyl)-6-ethyl-7-[[3-(trifluoromethyl)phenyl]methyl]-7H-pyrrolo[2,3-d]pyrimidin-4-yl]oxy]acetic acid methyl ester,

[[2-(methylthio)-5-(aminooxoacetyl)-6-ethyl-7-[[3-(trifluoromethyl)phenyl]methyl]-7H-pyrrolo[2,3-d]pyrimidin-4-yl]oxy]acetic acid,

[[2-(methylthio)-5-(aminooxoacetyl)-6-ethyl-7-[(3-chlorophenyl)methyl]-7H-pyrrolo[2,3-d]pyrimidin-4-yl]oxy]acetic acid methyl ester,

[[2-(methylthio)-5-(aminooxoacetyl)-6-ethyl-7-[(3-chlorophenyl)methyl]-7H-pyrrolo[2,3-d]pyrimidin-4-yl]oxy]acetic acid,

[[5-(aminooxoacetyl)-6-ethyl-7-[(3-chlorophenyl)methyl]-7H-pyrrolo[2,3-d]pyrimidin-4-yl]oxy]acetic acid methyl ester,

[[5-(aminooxoacetyl)-6-ethyl-7-[(3-chlorophenyl)methyl]-7H-pyrrolo[2,3-d]pyrimidin-4-yl]oxy]acetic acid,

[[5-(aminooxoacetyl)-6-ethyl-7-[[3-(trifluoromethyl)phenyl]methyl]-7H-pyrrolo(2,3-d]pyrimidin-4-yl]oxy]acetic acid methyl ester, and

[[5-(aminooxoacetyl)-6-ethyl-7-[[3-(trifluoromethyl)phenyl]methyl]-7H-pyrrolo[2,3-d]pyrimidin-4-yl]oxy]acetic acid.

12. A pharmaceutical formulation comprising a compound as claimed in claim 1 together with a pharmaceutically acceptable carrier or diluent therefor.

13. A method of treating a mammal to alleviate the pathological effects of Inflammatory Diseases; wherein the method comprises administration to said mammal of at least one compound as claimed in claim 1 in a pharmaceutically effective amount.

\* \* \* \* \*